(12) United States Patent
Nielsen et al.

(10) Patent No.: US 8,835,379 B2
(45) Date of Patent: Sep. 16, 2014

(54) DERIVATIVES OF CGRP

(75) Inventors: Anette Sams Nielsen, Lyngby (DK); Thomas Kruse, Herlev (DK); Janos Tibor Kodra, Koebenhavn O (DK); Jesper F. Lau, Farum (DK); Jacob Kofoed, Vaerloese (DK); Kirsten Raun, Lyngby (DK); Cecilia Nilsson, Uppsala (SE)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/501,872

(22) PCT Filed: Oct. 27, 2010

(86) PCT No.: PCT/EP2010/066216
§ 371 (c)(1),
(2), (4) Date: Jun. 14, 2012

(87) PCT Pub. No.: WO2011/051312
PCT Pub. Date: May 5, 2011

(65) Prior Publication Data
US 2012/0245083 A1    Sep. 27, 2012

Related U.S. Application Data

(60) Provisional application No. 61/259,341, filed on Nov. 9, 2009, provisional application No. 61/289,478, filed on Dec. 23, 2009, provisional application No. 61/362,476, filed on Jul. 8, 2010.

(30) Foreign Application Priority Data

Oct. 30, 2009 (EP) .................................. 09174673
Dec. 21, 2009 (EP) .................................. 09180154
Jul. 6, 2010 (EP) .................................. 10168560

(51) Int. Cl.
*A61K 38/00* (2006.01)
*C07K 14/575* (2006.01)
*A61K 47/48* (2006.01)

(52) U.S. Cl.
CPC ...... *C07K 14/57527* (2013.01); *A61K 47/48246* (2013.01); *A61K 47/48176* (2013.01); *A61K 47/48215* (2013.01); *A61K 47/48192* (2013.01)
USPC .......................................................... 514/1.1

(58) Field of Classification Search
CPC .................................. A61K 38/10; C07K 7/08
See application file for complete search history.

(56) References Cited

U.S. PATENT DOCUMENTS

| | | |
|---|---|---|
| 4,530,838 A | 7/1985 | Evans et al. |
| 4,720,483 A | 1/1988 | Jansz et al. |
| 4,804,742 A | 2/1989 | Neiss et al. |
| 2003/0204063 A1 | 10/2003 | Gravel et al. |
| 2004/0038861 A1 | 2/2004 | Cooper et al. |
| 2004/0091452 A1 | 5/2004 | Ekwuribe et al. |
| 2007/0203058 A1 | 8/2007 | Lau et al. |

FOREIGN PATENT DOCUMENTS

| | | |
|---|---|---|
| EP | 408294 A2 * | 1/1991 |
| EP | 2036923 | 3/2009 |
| WO | WO 90/07005 | 6/1990 |
| WO | WO 9012815 A1 * | 11/1990 |
| WO | WO 2007048026 A2 * | 4/2007 |
| WO | WO 2007/104789 | 9/2007 |
| WO | WO 2009030738 A1 * | 3/2009 |
| WO | 2009/156473 A1 | 12/2009 |

OTHER PUBLICATIONS

Frobert, Y. et al., "A Sensitive Sandwich Enzyme Immunoassay for Calcitonin Gene-Related Peptide (CGRP): Characterization and Application", Peptides, 1999, vol. 20, pp. 275-284.
Hermann-Rinke et al, "Calcitonin gene-related peptide potently stimulates glucagon-like peptide-1 release in the isolated perfused rat ileum" Peptides vol. 21(3): 431-437 (2000).

* cited by examiner

*Primary Examiner* — Marcela M Cordero Garcia
*Assistant Examiner* — Kaipeen Yang
(74) *Attorney, Agent, or Firm* — Jianjie Hu

(57) ABSTRACT

Acylated CGRP compounds with a linker have prolonged action and are valuable as medicaments.

11 Claims, 7 Drawing Sheets

SEQUENCE LISTING

```
<160> NUMBER OF SEQ ID NOS: 4

<210> SEQ ID NO 1
<211> LENGTH: 29
<212> TYPE: PRT
<213> ORGANISM: Artificial Sequence
<220> FEATURE:
<223> OTHER INFORMATION: human CGRP-alpha(8-36) fragment

<400> SEQUENCE: 1

Val Thr His Arg Leu Ala Gly Leu Leu Ser Arg Ser Gly Gly Val Val
1               5                   10                  15

Lys Asn Asn Phe Val Pro Thr Asn Val Gly Ser Lys Ala
            20                  25

<210> SEQ ID NO 2
<211> LENGTH: 29
<212> TYPE: PRT
<213> ORGANISM: Artificial Sequence
<220> FEATURE:
<223> OTHER INFORMATION: human CGRP-beta(8-36) fragment
```

```
<400> SEQUENCE: 2

Val Thr His Arg Leu Ala Gly Leu Leu Ser Arg Ser Gly Gly Met Val
1               5                   10                  15

Lys Ser Asn Phe Val Pro Thr Asn Val Gly Ser Lys Ala
            20                  25

<210> SEQ ID NO 3
<211> LENGTH: 37
<212> TYPE: PRT
<213> ORGANISM: Artificial Sequence
<220> FEATURE:
<223> OTHER INFORMATION: Modified CGRP
<220> FEATURE:
<221> NAME/KEY: MISC_FEATURE
<222> LOCATION: (1)..(1)
<223> OTHER INFORMATION: Ala or Ser
<220> FEATURE:
<221> NAME/KEY: MISC_FEATURE
<222> LOCATION: (3)..(3)
<223> OTHER INFORMATION: Asp or Asn
<220> FEATURE:
<221> NAME/KEY: MISC_FEATURE
<222> LOCATION: (5)..(5)
<223> OTHER INFORMATION: Ala or Ser
<220> FEATURE:
<221> NAME/KEY: MISC_FEATURE
<222> LOCATION: (8)..(8)
<223> OTHER INFORMATION: Val or Ala
<220> FEATURE:
<221> NAME/KEY: MISC_FEATURE
<222> LOCATION: (10)..(10)
<223> OTHER INFORMATION: His or Gln
<220> FEATURE:
<221> NAME/KEY: MISC_FEATURE
<222> LOCATION: (14)..(14)
<223> OTHER INFORMATION: Gly or Asp
<220> FEATURE:
<221> NAME/KEY: MISC_FEATURE
<222> LOCATION: (15)..(15)
<223> OTHER INFORMATION: Leu or Phe
<220> FEATURE:
<221> NAME/KEY: MISC_FEATURE
<222> LOCATION: (17)..(17)
<223> OTHER INFORMATION: Ser, Asn or Arg
<220> FEATURE:
<221> NAME/KEY: MISC_FEATURE
<222> LOCATION: (22)..(22)
<223> OTHER INFORMATION: Val, Ile, Met or Leu
<220> FEATURE:
<221> NAME/KEY: MISC_FEATURE
<222> LOCATION: (23)..(23)
<223> OTHER INFORMATION: Val, Ala, Leu or Gly
<220> FEATURE:
<221> NAME/KEY: MISC_FEATURE
<222> LOCATION: (24)..(24)
<223> OTHER INFORMATION: Lys, Ser, Asn or His
<220> FEATURE:
<221> NAME/KEY: MISC_FEATURE
<222> LOCATION: (25)..(25)
<223> OTHER INFORMATION: Ser, Asn, Asp or Pro
<220> FEATURE:
<221> NAME/KEY: MISC_FEATURE
<222> LOCATION: (26)..(26)
<223> OTHER INFORMATION: Asp or Asn
<220> FEATURE:
<221> NAME/KEY: MISC_FEATURE
<222> LOCATION: (31)..(31)
<223> OTHER INFORMATION: Asp or Asn
<220> FEATURE:
<221> NAME/KEY: MISC_FEATURE
<222> LOCATION: (33)..(33)
<223> OTHER INFORMATION: Gly or Ser
<220> FEATURE:
<221> NAME/KEY: MISC_FEATURE
<222> LOCATION: (34)..(34)
<223> OTHER INFORMATION: Ala or Ser
```

```
<220> FEATURE:
<221> NAME/KEY: MISC_FEATURE
<222> LOCATION: (35)..(35)
<223> OTHER INFORMATION: Glu, Gln, Lys or Asn
<220> FEATURE:
<221> NAME/KEY: MISC_FEATURE
<222> LOCATION: (36)..(36)
<223> OTHER INFORMATION: Ala or Ser

<400> SEQUENCE: 3

Xaa Cys Xaa Thr Xaa Thr Cys Xaa Thr Xaa Arg Leu Ala Xaa Xaa Leu
1               5                   10                  15

Xaa Arg Ser Gly Gly Xaa Xaa Xaa Xaa Phe Val Pro Thr Xaa Val
            20                  25                  30

Xaa Xaa Xaa Xaa Phe
        35

<210> SEQ ID NO 4
<211> LENGTH: 37
<212> TYPE: PRT
<213> ORGANISM: Artificial Sequence
<220> FEATURE:
<223> OTHER INFORMATION: Modified CGRP
<220> FEATURE:
<221> NAME/KEY: MISC_FEATURE
<222> LOCATION: (1)..(1)
<223> OTHER INFORMATION: Ala or Ser
<220> FEATURE:
<221> NAME/KEY: MISC_FEATURE
<222> LOCATION: (3)..(3)
<223> OTHER INFORMATION: Asp or Asn
<220> FEATURE:
<221> NAME/KEY: MISC_FEATURE
<222> LOCATION: (14)..(14)
<223> OTHER INFORMATION: Asp or Gly
<220> FEATURE:
<221> NAME/KEY: MISC_FEATURE
<222> LOCATION: (17)..(17)
<223> OTHER INFORMATION: Arg or Ser
<220> FEATURE:
<221> NAME/KEY: MISC_FEATURE
<222> LOCATION: (22)..(22)
<223> OTHER INFORMATION: Val or Met
<220> FEATURE:
<221> NAME/KEY: MISC_FEATURE
<222> LOCATION: (23)..(23)
<223> OTHER INFORMATION: Val or Leu
<220> FEATURE:
<221> NAME/KEY: MISC_FEATURE
<222> LOCATION: (25)..(25)
<223> OTHER INFORMATION: Asp, Asn or Ser
<220> FEATURE:
<221> NAME/KEY: MISC_FEATURE
<222> LOCATION: (31)..(31)
<223> OTHER INFORMATION: Asp or Asn
<220> FEATURE:
<221> NAME/KEY: MISC_FEATURE
<222> LOCATION: (35)..(35)
<223> OTHER INFORMATION: Glu or Lys

<400> SEQUENCE: 4

Xaa Cys Xaa Thr Ala Thr Cys Val Thr His Arg Leu Ala Xaa Leu Leu
1               5                   10                  15

Xaa Arg Ser Gly Gly Xaa Xaa Lys Xaa Asn Phe Val Pro Thr Xaa Val
            20                  25                  30

Gly Ser Xaa Ala Phe
        35
```

DERIVATIVES OF CGRP

CROSS-REFERENCE TO RELATED APPLICATIONS

This application is a 35 U.S.C. 371 national stage application of International Patent Application PCT/EP2010/066216 (published as WO 2011/051312 A1), filed Oct. 27, 2010, which claimed priority of European Patent Application 09174673.5, filed Oct. 30, 2009, European Patent Application 09180154.8, filed Dec. 21, 2009, and European Patent Application 10168560.0, filed Jul. 6, 2010; this application further claims priority under 35 U.S.C. 119 of U.S. Provisional Application 61/259,341, filed Nov. 9, 2009, U.S. Provisional Application 61/289,478, filed Dec. 23, 2009, and U.S. Provisional Application 61/362,476, filed Jul. 8, 2010.

FIELD OF THIS INVENTION

The present invention relates to novel derivatives of CGRP and aspects related thereto.

BACKGROUND OF THIS INVENTION

The metabolic syndrome is manifested by obesity, insulin resistance, dyslipidaemia and hypertension. Today, the four manifestations are treated by selective treatment paradigmes.

Calcitonin gene-related peptide (hereinafter designated CGRP) is a peptide which, in several species, exists in two forms, designated CGRP-alpha and CGRP-beta (or CGRP-I and CGRP-II, respectively). CGRP peptides are highly conserved within species. For example, the amino acid sequences of human and rat CGRP peptides are mentioned in table 1 in Peptides 20 (1999), 275-84. CGRP is released from, e.g., sensory, motor and enteric nerves.

From the literature it is evident that CGRP triggers various pharmacological effects, e.g.: 1) vasodilation, 2) muscle and liver AMP kinase (AMPK) activation and lipolysis and/or fat oxidation, 3) reduction in food intake, 4) inhibition of gastric emptying and modification of gut function and 5) increasing glycolysis and inhibition of glycogen synthesis. The net physiological significance of the referred effects is not completely understood and no results of chronic CGRP exposure exists (e.g. fasting insulin, HbA1C and sustained vasodilation). Whereas AMPK activation, fat oxidation and reduced food intake may be beneficial in metabolic diseases, glycolysis and inhibition of glycogen synthesis has been suggested to mediate insulin resistance.

Native CGRP has a half life of less than 30 minutes and a short duration of pharmacological actions after CGRP infusions is evident. Due to vasodilatory effects of administered CGRP, in vivo pharmacological studies of native CGRP are contaminated with effects secondary to vasodilation and to compensatory vasoconstrictive actions. Thus, the vasodilatory action is the dose limiting action of CGRP which prevents the complete understanding of the actions relevant to metabolic syndrome. Thus, the pharmacological usefulness of CGRP requires the generation of CGRP analogues with prolonged action and some effects may even only be obtained with prolonged analogues.

Claim 1 in US 2003/0204063 relates to a peptide substituted by 1-5 conformationally rigid moieties selected among six general groups of groups with many possible substituents. In claim 2 therein, 55 peptides are exemplified, for example, CGRP. None of the working examples deals with modified CGRP. According to claim 25 therein, modified CGRP has at least one conformational rigid moiety.

OBJECTS OF THIS INVENTION

The object of this invention is to overcome or ameliorate at least one of the disadvantages of the prior art, or to provide a useful alternative.

Another aspect of this invention relates to the furnishing of compounds having pharmacological properties similar to those of CGRP and which cause prolonged action compared with those caused by CGRP.

Another aspect of this invention relates to the furnishing of compounds causing improved pharmacokinetic properties compared with those caused by CGRP.

Another aspect of this invention relates to the furnishing of compounds causing improved pharmacodynamic properties compared with those caused by CGRP.

Another aspect of this invention relates to the furnishing of compounds causing higher plasma GLP-1 values than those caused by CGRP.

Another aspect of this invention relates to the furnishing of compounds inducing GLP-1 release in vivo.

Another aspect of this invention relates to the furnishing of compounds which cause release of GLP-1 from cultured L-cells.

Another aspect of this invention relates to the furnishing of compounds causing a reduction in food intake compared with that caused by CGRP.

Another aspect of this invention relates to the furnishing of compounds causing an increase in energy expenditure compared with that caused by CGRP.

Another aspect of this invention relates to the furnishing of compounds causing an increase in weight loss compared with that caused by CGRP.

Another aspect of this invention relates to the furnishing of compounds causing a reduction in the blood pressure compared with that caused by CGRP.

Another aspect of this invention relates to the furnishing of compounds which, to a large degree or fully, have the same pharmacological properties as CGRP has.

Another aspect of this invention relates to the furnishing of compounds causing reduction in plasma, muscle and liver triglyceride.

Another aspect of this invention relates to the furnishing of compounds causing a reduced level of HbA1c.

Another aspect of this invention relates to the furnishing of compounds causing a reduced level of fasting insulin.

Another aspect of this invention relates to the furnishing of compounds which causes a sustained reduction in blood pressure.

Another aspect of this invention relates to the furnishing of compounds which causes improved insulin sensitivity in pre-diabetic and diabetic animal models.

Another aspect of this invention relates to the furnishing of compounds which causes increased glycolysis in mammalian cells.

Another aspect of this invention relates to the furnishing of compounds which causes increased AMPK activation in mammalian cells.

DEFINITIONS

Herein, the term CGRP compounds covers compounds of the general formula I:

$$X_1CX_2TX_3TCX_4TX_5RLAX_6X_7LX_8RSGGX_9X_{10}X_{11}X_{12}X_{13}FVPTX_{14}VX_{15}X_{16}X_{17}X_{10}F \quad \text{(I)}$$

wherein $X_1$ is Ala or Ser, $X_2$ is Asp or Asn, $X_3$ is Ala or Ser, $X_4$ is Val or Ala, $X_5$ is His or Gln, $X_6$ is Gly or Asp, $X_7$ is Leu or Phe, $X_8$ is Ser, Asn or Arg, $X_9$ is Val, Ile, Met or Leu, $X_{10}$ is Val, Ala, Leu or Gly, $X_{11}$ is Lys, Ser, Asn or His, $X_{12}$ is Ser, Asn, Asp, Pro, $X_{13}$ is Asp or Asn, $X_{14}$ is Asp or Asn, $X_{15}$ is Gly or Ser, $X_{16}$ is Ala or Ser, $X_{17}$ is Glu, Gln, Lys or Asn, $X_{18}$ is Ala or Ser, and the carboxy group in the C terminal amino acid residue is, optionally, amidated, and, in formula I, the specific amino acid residues are indicated by the usual one letter codes for the amino acids. Formula I covers, for example, CGRP from the following species: pig, sheep, laughing frog, human, mouse, horse, dog, rat, two-colored leaf frog, Japanese rice fish, Japanese gecko, Japanese buffer fish and salmon; all in alpha and beta form, where applicable. For several species, CGRP exists both in an alpha and a beta form and both forms are herein considered CGRP compounds. One subgroup of compounds of formula I is compounds of the general formula II:

  (II)

wherein $X_1$ is Ala or Ser, $X_2$ is Asp or Asn, $X_6$ is Asp or Gly, $X'_8$ is Arg or Ser, $X'_9$ is Val or Met, $X'_{10}$ is Val or Leu, $X'_{12}$ is Asp, Asn or Ser, $X_{14}$ is Asp or Asn, $X'_{17}$ is Glu or Lys, and the carboxy group in the C terminal amino acid residue is, optionally, amidated. Formula II covers, for example, CGRP from the following species: pig, mouse, human, dog and rat; all in alpha and beta form, where applicable. Specifically, the term "CGRP compound" covers human CGRP-alpha, human CGRP-beta, rat CGRP-alpha and rat CGRP-beta and analogues of human CGRP-alpha, of human CGRP-beta, of rat CGRP-alpha and of rat CGRP-beta.

The term "CGRP compounds" also covers analogues of compounds of the general formula I or II.

Herein, "analogues of compounds of the general formula I or II" are compounds of the general formula I or II, wherein one, two or three of the amino acid residues is exchanged with another amino acid residue, an amino acid residue is omitted or a further amino acid residue is inserted.

In one embodiment, an "analogue of a compound of the general formula I or II" is a compound of the general formula I or II, wherein one, two or three of the amino acid residues is exchanged with another amino acid residue.

In one embodiment, an "analogue of a compound of the general formula I or II" is a compound of the general formula I or II, wherein one of the amino acid residues is exchanged with another amino acid residue.

In one embodiment, an "analogue of a compound of the general formula I or II" is a compound of the general formula I or II, wherein two of the amino acid residues are exchanged with another amino acid residue.

In one embodiment, an "analogue of a compound of the general formula I or II" is a compound of the general formula I or II, wherein three of the amino acid residues are exchanged with another amino acid residue.

In one embodiment, an "analogue of a compound of the general formula I or II" is a compound of the general formula I or II wherein an amino acid residue is omitted.

In one embodiment, an "analogue of a compound of the general formula I or II" is a compound of the general formula I or II wherein a further amino acid residue is inserted.

The amino acid numbering of an analogue of a compound of the general formula I or II conforms with the amino acid numbering in the compound of the general formula I or II. Preferably, the amino acid residues inserted are amino acids which can be coded for by a nucleic acid (the genetic triplet).

Furthermore, the term "CGRP compounds" also covers the above mentioned CGRP compounds with conservative substitution.

Herein, "conservative substitution", when describing a protein, refers to a change in the amino acid composition of the protein in which a residue is replaced with a structurally similar substitute that does not substantially alter the protein's activity. Thus, a "conservatively substituted variant" of a particular amino acid sequence refers to an amino acid substitution of an amino acid that is not critical for protein activity, or substitution of an amino acid with another amino acid having similar properties (for example, acidic, basic, positively or negatively charged, polar or non-polar, etc.) such that the substitution of even critical amino acid do not substantially alter activity. Conservative substitution tables providing functionally similar amino acids are well known in the art. The following six groups each contain amino acids that are conservative substitutions for one another: 1) alanine, serine and threonine, 2) aspartic acid and glutamic acid, 3) asparagine and glutamine, 4) arginine and lysine, 5) isoleucine, leucine, methionine and valine, and 6) phenylalanine, tyrosine and tryptophan. One of skill in the art will appreciate that the above-identified substitutions are not the only possible conservative substitutions. For example, one may regard all charged amino acids as conservative substitutions for each other whether they are positive or negative. In addition, individual substitutions, deletions or additions which alter, add or delete a single amino acid or a small percentage of amino acids in an encoded sequence can also be "conservatively substituted variants."

Said CGRP compounds have the usual intramolecular disulphide bridge between the two Cys residues (usually in positions 2 and 7).

Herein, the terms "h-CGRP-alpha", "h-CGRP-beta", "r-CGRP-alpha" and "r-CGRP-beta" are abbreviations of human CGRP-alpha, human CGRP-beta, rat CGRP-alpha and rat CGRP-beta, respectively.

Herein, the terms "h-CGRP-I", "h-CGRP-II", "r-CGRP-I" and "r-CGRP-II" are synonyms of human CGRP-alpha, human CGRP-beta, rat CGRP-alpha and rat CGRP-beta, respectively.

Herein, a term like "h-CGRP-alpha(2-37)" covers the peptide consisting of the amino acid residues in positions 2 through 37 in h-CGRP-alpha and similarly for the indication of other positions.

Herein, the term "amino acid residue" covers an amino acid from which, formally, a hydroxy group has been removed from a carboxy group and/or from which, formally, a hydrogen atom has been removed from an amino group.

Herein, a term like "Ser1" means that the amino acid residue Ser is at position 1 of the CGRP compound (counted from the N-terminal end). Likewise, "Cys2" means that the amino acid Cys is in position 2 of the CGRP compound (counted from the N-terminal end) and similarly for the other positions.

Examples of amino acids which can be coded for by a nucleic acid are (with the usual three letter codes & one letter codes in parenthesis): alanine (Ala & A), arginine (Arg & R), asparagine (Asn & N), aspartic acid (Asp & D), cysteine (Cys & C), glutamic acid (Glu & E), glutamine (Gln & Q), glycine (Gly & G), histidine (His & H), isoleucine (Ile & I), leucine (Leu & L), lysine (Lys & K), methionine (Met & M), phenylalanine (Phe & F), proline (Pro & P), serine (Ser & S), threonine (Thr & T), tryptophan (Trp & W), tyrosine (Tyr & Y) and valine (Val & V). If, due to typing errors, there are deviations from the commonly used codes, the commonly used codes apply.

Herein, the expression that an acylated derivative according to the present invention has a "prolonged action" means that the T½ thereof is at least 50%, preferably at least 100%, and more preferred at least 500%, longer than the T½ of the corresponding non-derivatised CGRP. T½ is the half life time determined by the method described in the chapter below with the heading "Pharmacokinetic and GLP-1-release properties of CGRP and analogues thereof".

"Albumin binding affinity" may be determined by several methods known within the art. In one method, the compound to be measured is radiolabeled with, for example, $^{125}$I or $^3$H and incubated with immobilized albumin (*Biochem. J.*, 312 (1995), 725-31). The binding of the compound relative to a standard is calculated. In another method, a related compound is radiolabeled and its binding to albumin immobilized on, for example, SPA beads is competed by a dilution series of the derivative to be measured. The $EC_{50}$ value for the competition is a measure of the affinity of the derivative. In a third method, the receptor affinity or potency of a compound is measured at different concentrations of albumin, and the shift in relative affinity or potency of the compound as a function of albumin concentration reflects its affinity for albumin.

Herein, the term "pharmacokinetic properties" covers Cmax and T½.

Herein, the term "pharmacodynamic properties" covers reduction in blood pressure, increase in plasma GLP-1 levels, reduction in food intake, weight loss, increased lipid oxidation, increased glycolysis, reduced plasma and tissue TG level, increased energy expenditure, reduced fasting insulin levels, reduced HbA1c levels and increased insulin sensitivity.

Herein, "GLP-1" is the so-called glucagon-like peptide 1 consisting of 37 amino acid residues.

Herein, "total GLP-1" is GLP-1 and its primary DDP-IV metabolite GLP-1(7-37).

Herein, "therapeutically effective amount" refers to a predetermined amount of an agent calculated to elicit the biological or medical response of a tissue, system, animal or human that is being sought by the researcher, veterinarian, physician or other clinician, for example, an amount sufficient to stimulate, prevent, hinder, retard or reverse the progression of a disease or any other undesirable symptoms to achieve a desired therapeutic effect.

Herein, "pharmaceutically acceptable carrier" or "pharmaceutically acceptable excipient" refers to a carrier that does not cause an adverse physical reaction upon administration and one in which a therapeutic agent is sufficiently soluble to deliver a therapeutically effective amount. Examples of excipients include buffered water, physiological saline, phosphate buffered saline (PBS), dextrose solution, Hank's solution and inert diluents, such as calcium carbonate, sodium carbonate, lactose, calcium phosphate or sodium phosphate.

Herein, "mammal" has its usual meaning and includes primates (for example, humans and non-human primates), experimental animals (for example, rodents such as mice and rats), farm animals (such as cows, hogs, sheep and horses), and domestic animals (such as dogs and cats).

Herein, the terms "treatment" or "treating" of a condition and/or a disease in a mammal, means (i) preventing the condition or disease, that is, avoiding any clinical symptoms of the disease; (ii) inhibiting the condition or disease, that is, arresting the development or progression of clinical symptoms; and/or (iii) relieving the condition or disease, that is, causing the regression of clinical symptoms.

Herein, "$EC_{50}$" has its normal meaning in the art and refers to a concentration of a compound that results in 50% of maximum enhancement of a specified biological effect, for example, the concentration at which a biological effect is at one-half of its maximum value.

SUMMARY OF THE INVENTION

This invention relates to acylated CGRP compounds.

BRIEF DESCRIPTION OF THE FIGURES

In the figures and in text related thereto, "Analog alpha1" and "Analog beta1" are compounds of this invention which are specifically mentioned in examples 1 and 2, respectively, below. Furthermore, in the figures, "alpha-CGRP" and beta-CGRP" are human CGRP-alpha and human CGRP-beta, respectively.

SEQUENCE LISTS

Figure 1:
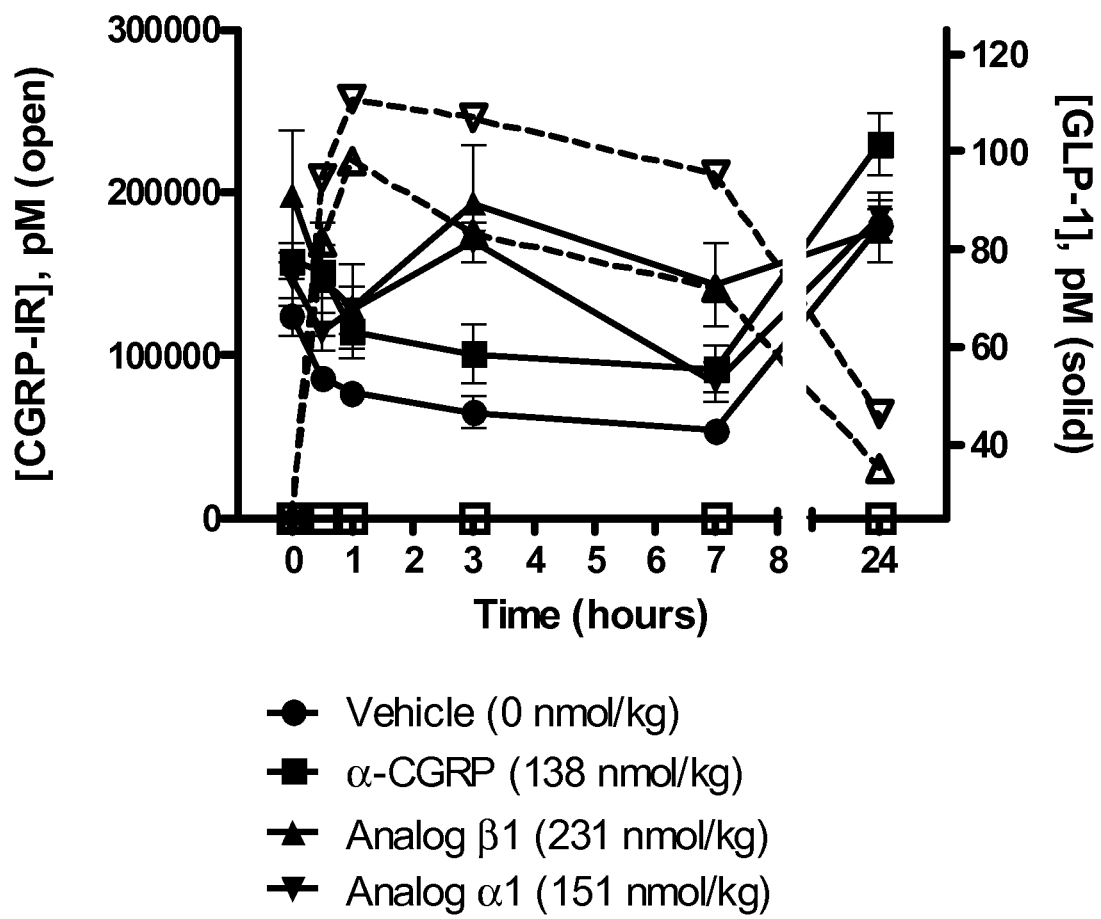
FIG. 1. Pharmacokinetic profile and simultaneous effect on plasma GLP-1 of alpha-CGRP, Analog alpha1 and Analog beta1. SD rats were dosed subcutaneously (hereinafter designated s.c.) with CGRP or a compound of this invention. Plasma samples were analyzed for CGRP and total GLP-1 by ELISA protocols. Data are given as mean±SEM, n=6. Open symbols represents exposure data (left Y-axis) and solid symbols represents plasma GLP-1 levels (right Y-axis).

SEQ ID NO. 1 is the human CGRP-alpha(8-36) sequence present in the compounds prepared in examples 1 & 3 and SEQ ID NO. 2 is the human CGRP-beta(8-36) sequence present in the compound prepared in example 2, mentioned below.

SEQ ID NO. 3 is the general formula I and SEQ ID NO. 4 is the general formula II, mentioned below.

DETAILED DESCRIPTION OF THIS INVENTION

In one aspect, the present invention relates to compounds of the general formula X—Y—Z, wherein X designates a CGRP compound from which, formally, a hydrogen has been removed from one of the amino groups present in an amino acid residue; Y is a linker as defined herein; and Z is an acyl group; wherein the —Y—Z moiety is connected to an amino group present in an amino acid residue present in the CGRP compound.

In the compounds of this invention, the acyl group (designated Z) and/or the acyl group connected to the linker (designated Y) shall have a sufficient albumin binding affinity.

The linker, Y, is elected from the group consisting of the six groups of the following formulae:

The compounds of this invention can be prepared in a manner known per se.

One strategy could be first to prepare the CGRP compound. The production of polypeptides, for example, GLP-1, insulins and growth hormone, is well known in the art. A CGRP compound may for instance be produced by classical peptide synthesis, for example, solid phase peptide synthesis using t-Boc or Fmoc chemistry or other well established techniques, see, for example, Greene and Wuts, "Protective Groups in Organic Synthesis", John Wiley & Sons, 1999.

The palate of pharmacological effects of the compounds of this invention is beneficial for the treatment of metabolic syndrome, diabetes, obesity and cardiovascular disease, exclusively since they have a prolonged action.

In one embodiment, the compounds of this invention shall have a sufficient potency at the CGRP receptor. The potency can be determined by the method described in the chapter below with the heading: "CGRP-induced cAMP accumulation in CGRP receptor expressing cells". Preferably, the potency shall be at least 1% of that of human CGRP-alpha, more preferred at least 10% of that of human CGRP-alpha, even more preferred at least 50% of that of human CGRP-alpha.

In one embodiment, the compounds of this invention shall give a sufficient in vivo release of GLP-1. The release of GLP-1 in vivo can be determined by the method described in the chapter below with the heading: "Pharmacokinetic and GLP-1-release properties of CGRP and analogues thereof".

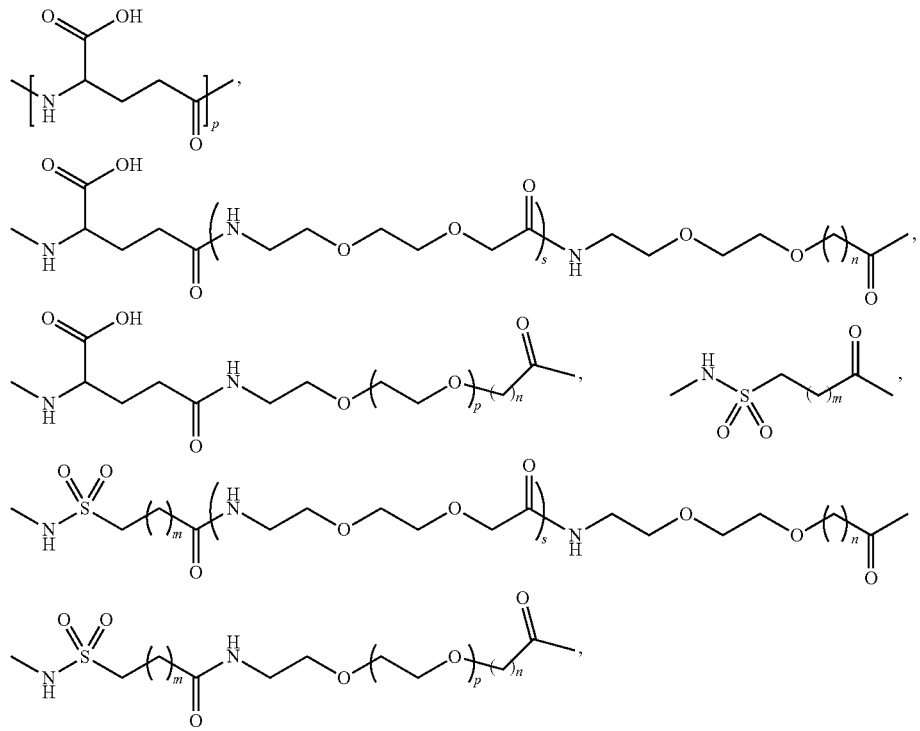

and
wherein m is 0, 1, 2, 3, 4, 5 or 6; n is 1, 2 or 3; s is 0, 1, 2 or 3; and p is 1, 2, 3, 4, 5, 6, 7, 8, 9, 10, 11, 12, 13, 14, 15, 16, 17, 18, 19, 20, 21, 22 or 23, and wherein the carbonyl end of these moieties is connected to the CGRP compound (designated X) and the amino end of these moieties is connected to the acyl group (designated Z).

Preferably, the concentration of plasma total GLP-1 in vivo shall be at least 5% increased as compared to that of the vehicle, more preferred at least 20% increased as compared to that of the vehicle, even more preferred at least 75% increased as compared to that of the vehicle.

In one embodiment, the compounds of this invention shall have a sufficient effect on the food intake. In another embodiment of this invention, the compounds of this invention shall cause weight reduction. The effect on the food intake can be determined by the method described in the chapter below with the heading: "CGRP-induced reduction in food intake by automatic food intake measurements (FeedWin)". Preferably, the effect on the food intake shall be at least 2% reduction, more preferred at least 10% reduction, even more preferred at least 25% reduction.

In one embodiment, the compounds of this invention shall have a sufficient effect on blood pressure. The effect on the blood pressure can be determined by the method described in the chapter below with the heading: "Continuous detection of blood pressure". Preferably, the effect on the blood pressure shall be at least 1%, more preferred at least 5%, even more preferred at least 10%.

In one embodiment, the compounds of this invention shall have a sufficient effect on HbA1C after 3 weeks treatment. In another embodiment of this invention, the compounds of this invention shall cause reduction in HbA1c level after prolonged exposure. The effect on the HbA1C level can be determined by the method described in the chapter below with the heading: "Plasma insulin and HbA1c after subcronic administration in ob/ob mice". Preferably, the effect on HbA1c shall be at least 0.2%, more preferred at least 1%, even more preferred at least 2%.

In one embodiment, the compounds of this invention shall have a sufficient effect on fasting insulin after 3 weeks treatment. In another embodiment of this invention, the compounds of this invention shall cause reduction in fasting insulin levels. The effect on the fasting insulin level can be determined by the method described in the chapter below with the heading: "Plasma insulin and HbA1c after subcronic administration in ob/ob mice". Preferably, the effect on fasting insulin shall be at least 50 pM, more preferred at least 100 pM, even more preferred at least 150 pM.

In one embodiment, the compounds of this invention shall cause sustained vasodilatation. Sustained vasodilation means reduction in blood pressure lasting for at least 12 hours.

In one embodiment, the compounds of this invention shall cause increased energy expenditure. Preferably, the increased energy expenditure shall be at lest 4%.

The compounds of this invention have unique pharmacological effects. Pharmocological formulations containing a compound of this invention can, for example, be used for 1) vasodilation, 2) muscle and liver AMP kinase activation and lipolysis and/or fat oxidation, 3) reduction in food intake, 4) inhibition of gastric emptying 5) increased energy expenditure 6) reduce T2D associated elevated fasting insulin, 7) reduce HbA1c levels and 8) reduce body weight. Hence, pharmacological treatment with a compound of this invention may be suitable for the treatment or prevention of metabolic syndrome, diabetes, obesity and cardiovascular disease, e.g., hypertension. Due to vasodilatory effects of the administration of a compound of this invention, in vivo pharmacological studies using a compound of this invention are often contaminated with effects secondary to vasodilation and compensatory vasoconstrictive actions. Thus, the vasodilatory action may be a dose limiting action when using a compound of this invention.

Pharmacological Formulations

In one aspect, according to this invention, a therapeutically effective amount of a compound of this invention is administered to a subject (for example, patient or animal) who would benefit from such a treatment. The treatment could, for example, be insulin resistance, type-2 diabetes mellitus, hypertension, obesity, dyslipidaemia, atherosclerosis and thrombosis. The dosage ranges for the administration of the compound of this invention are those large enough to produce the desired effect.

In a related aspect, this invention provides a compound of this invention in a unit dosage form for administration to patients. As used herein, "unit dosage form" refers to a composition intended for a single administration to treat a subject suffering from a disease or medical condition. Each unit dosage form typically comprises each of the compounds of this invention plus pharmaceutically acceptable excipients. Examples of unit dosage forms are individual tablets, individual capsules, bulk powders, liquid solutions, suppositories, emulsions or suspensions. Treatment of the disease or condition may require periodic administration of unit dosage forms, for example: one unit dosage form two or more times a day, one with each meal, one every four hours or other interval, or only one per day. Formulations for injection may be presented in unit dosage form, for example, in ampoules or in multidose containers.

The unit dosage form of the invention contains a therapeutically effective dose of a compound of this invention. In an embodiment, administration of the unit dosage form results in a proper level of a compound of this invention in the mammal. In an embodiment, the dose results in only minimal increase (if any) in blood or plasma lactate and glucose levels or vasodilatation.

Although the particular dose will depend on the molecular structure and chemical properties of the particular compound of this invention, those of skill in the pharmacology art will understand from the disclosure herein that appropriate doses can be determined using routine techniques. For example, a dose or formulation of a compound of this invention with no or only minimally eliciting an undesired side-effect in the mammal (for example, an increased level of in blood glucose, blood lactate, or vasodilatation in the mammal) can be determined in a variety of ways. As used in this context, "an increased level" can refer to an increase to a predetermined level (for example, a designated threshold level of the side effect). One method for making such determination involves conducting dose-response assays by (a) administering a plurality of different doses (or formulations) of a compound of this invention to test mammals; and (b) measuring the effect of each dose or formulation and measuring the effect of each dose on the side-effect, thereby creating dose-response data for the desired effect lipolysis and the side-effect; and, (ii) determining from the dose-response data a dose of the a compound of this invention formulation that gives the desired effect but does not elicit the side-effect.

Usually the doses for a compound of this invention would fall in a concentration of from $10^{-15}$ M to $10^{-5}$ M (for example, as measured in one or more of muscle, blood, serum or plasma). As noted above, in the case of a compound of this invention, a dose that results in a plasma or serum concentration of the compound of this invention in the $EC_{50}$ range for the compound of this invention ($10^{-13}$ M to $10^{-10}$ M) is particularly useful.

The amount of a compound of this invention administered to an animal to achieve a desired level or concentration of the compound of this invention will depend on a number of factors well know to practitioners, such as compound half-life (for example, serum half-life), and the frequency and mode of administration. For illustration and not limitation, the dose of a compound of this invention may be administered in the range from 20 picograms to 1 gram, more often between 3 nanograms and 50 micrograms daily. In various embodiments, the unit dosage (in some cases daily dosage) is less than about 10 micrograms, less than about 1 microgram, less than about 100 nanograms, less than about 10 nanograms, less than about 1 nanogram, less than about 100 picograms, or less than about 10 picograms.

Other ranges of a compound of this invention will be apparent to the skilled practitioner based on data from initial dose-response curves and other data that can be obtained by routine methods.

The invention also provides a composition containing a compound of this invention combined with a pharmaceutically acceptable excipient. In one embodiment, a compound of this invention and excipient are formulated.

A compound of this invention can be formulated or coadministered with other active agents (for example, agents that alone or in combination with a compound of this invention, reduce lipid, free fatty acid, and/or long chain CoA levels). It is contemplated that, in an embodiment, a compound of this invention is not coadministered with insulin.

A compound of this invention can be directly administered to the host to be treated. Administration is optionally under sterile conditions. However, while it is possible for a compound of this invention to be administered alone, it is often preferable to present it as a pharmaceutical formulation. Formulations typically comprise at least one active ingredient together with one or more acceptable carriers thereof. Each carrier should be both pharmaceutically and physiologically acceptable in the sense of being compatible with the other ingredients and not injurious to the subject. Therapeutic formulations can be prepared by any methods well known in the art of pharmacy.

A compound of this invention may be administered by oral, parenteral (for example, intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. Often, the administration will be parenterally (for example, intravenous or s.c. (subcutaneous)).

If desired (for example, to maintain a particular plasma concentration) a compound of this invention can be administered to patients in the form of controlled delivery formulations. A variety of suitable controlled delivery systems are known, including forms suitable for oral, parenteral, and other routes of administration. Excipients employed in the manufacture of drug delivery systems are described in various publications known to those skilled in the art. The US Pharmacopoeia provides many examples of modified-release oral dosage forms. This publication also presents general chapters and specific tests to determine the drug release capabilities of extended-release and delayed-release tablets and capsules. In one aspect of the invention, a compound of this invention is administered in conjunction with a program of exercise, to enhance exercise-mediated breakdown of triglycerides in a subject.

The pharmaceutical compositions may be in the form of a sterile injectable aqueous or oleagenous suspension. This suspension may be formulated according to the known art using those suitable dispersing or wetting agents and suspending agents. The sterile injectable preparation may also be a sterile injectable solution or suspension in a non-toxic parenterally-acceptable diluent or solvent. Among the acceptable vehicles and solvents that may be employed are water, Ringers solution and isotonic sodium chloride solution. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, and the severity of the particular condition. In some embodiments, daily or weekly administration of a compound of this invention is contemplated.

CONCLUSIONS FROM THE DRAWINGS

Based upon FIG. 1, it can be concluded that analogues with improved pharmacokinetic properties (T½ and Cmax) as compared to human CGRP-alpha have been synthesized and that these compounds cause increased GLP-1 plasma levels after administration.

Figure 2:
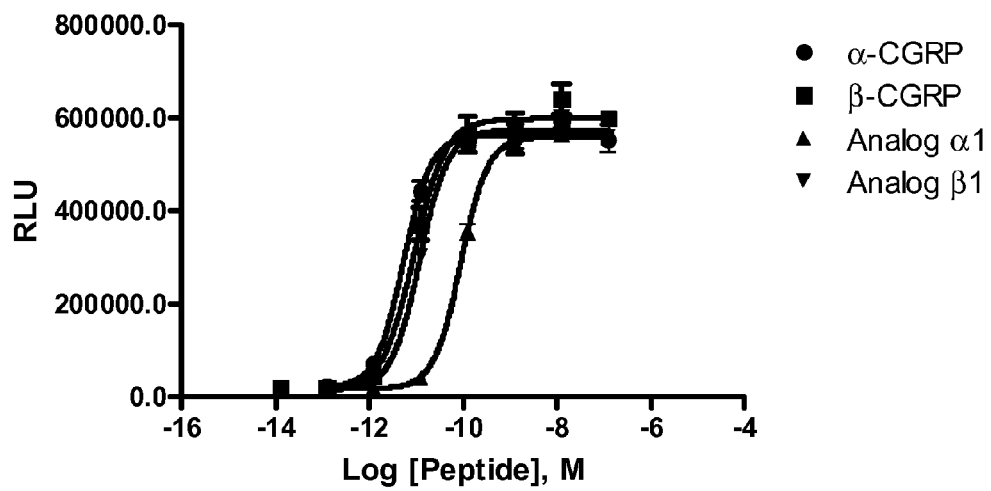
FIG. 2. Dose-response curves (cAMP accumulation in CGRP-receptor expressing cells). Cyclic AMP accumulation induced by CGRP and compounds of this invention in CGRP-receptor expressing cells. Dose-response curves were fitted by use of GraphPad Prism software and $pEC_{50}$ values were calculated. Data are given as mean±SEM, n=2.

Based upon FIG. 2, it can be concluded that CGRP analogues equipotent with human CGRP-alpha and with lower potency than human CGRP-alpha has been synthesized.

Figure 3:
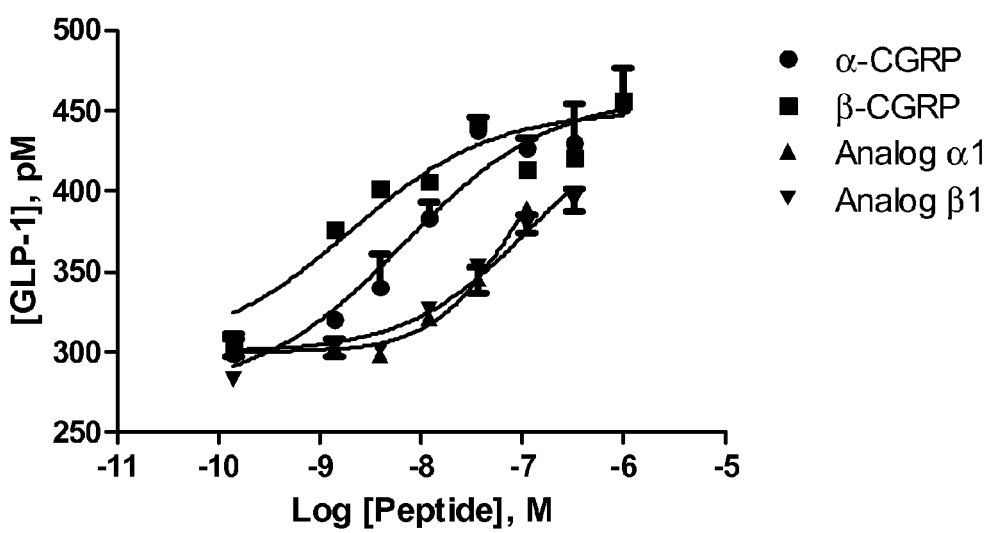
FIG. 3. CGRP-induced GLP-1 release in gut L-cell line. L-cells (50.000 cells/well) were stimulated with CGRP in serum free culture medium with 0.1% bovine serum albumin (hereinafter designated BSA) and 0.005% tween20 for 3 hours and media were analysed for the content of GLP-1 by use of ELISA. Data are given as mean±SEM, n=2.

Based upon FIG. 3, it can be concluded that CGRP and CGRP analogues stimulate release of GLP-1 from a murine intestinal L-cell line.

Figure 4:
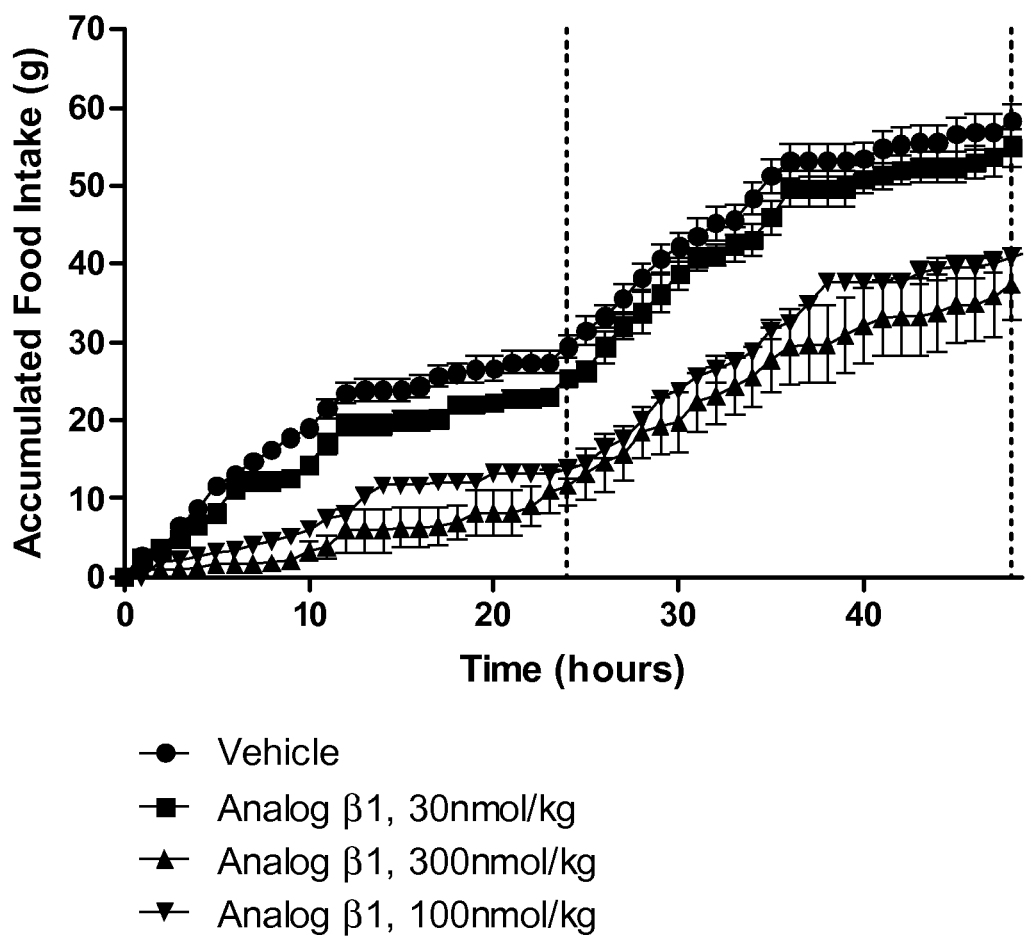
FIG. 4. Reduction in accumulated food intake induced by compounds of this invention (Analog beta1). Data are given as mean±SEM, n=5-8. Food intake was monitored for 48 hours in FeedWin setup for SD rats dosed s.c. with compounds of this invention or vehicle.

Based upon FIG. 4, it can be concluded that an analogue of beta-CGRP causes a dose dependent reduction in cumulative food intake in SD rats.

Figure 5:
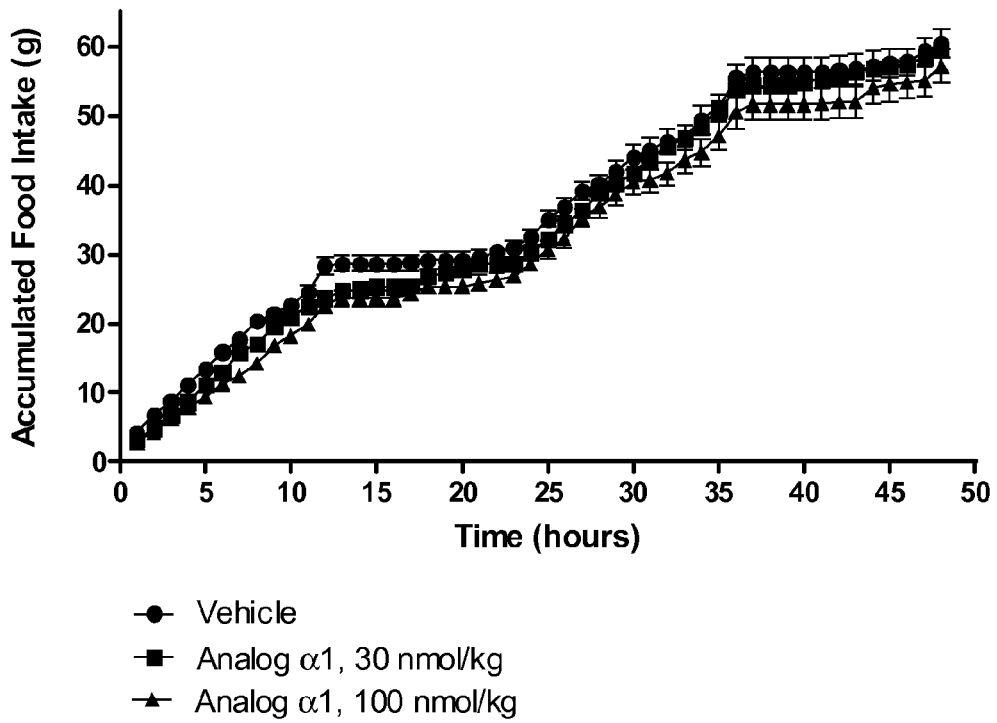
FIG. 5. Reduction in accumulated food intake induced by compounds of this invention (Analog alpha1). Data are given as mean±SEM, n=5-8. Food intake was monitored for 48 hours in FeedWin setup for SD rats dosed intra peritoneal (herein designated i.p.) with compounds of this invention or vehicle.

Based upon FIG. 5, it can be concluded that an analogue of alpha-CGRP causes a dose dependent reduction in cumulative food intake in SD rats.

Figure 6:
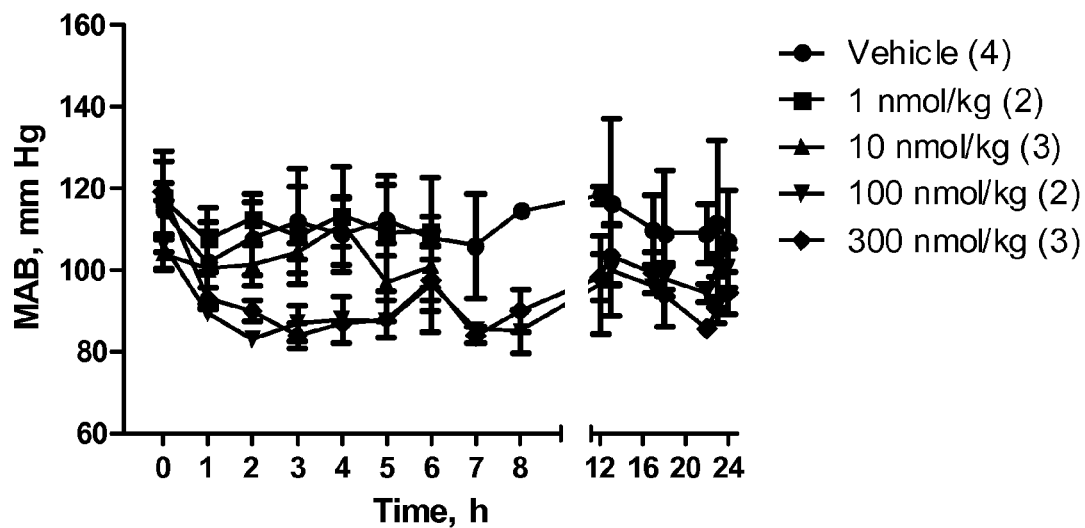
FIG. 6. Effect on mean arterial blood pressure (MAB) by Analog beta1 after s.c. injection in SD rats. Data are given as mean±SEM (n=2-4). MAB was determined in continuously by telemetry.

Based upon FIG. 6, it can be concluded that an analogue of beta-CGRP causes a dose dependent and sustained reduction in blood pressure in SD rats.

Figure 7:
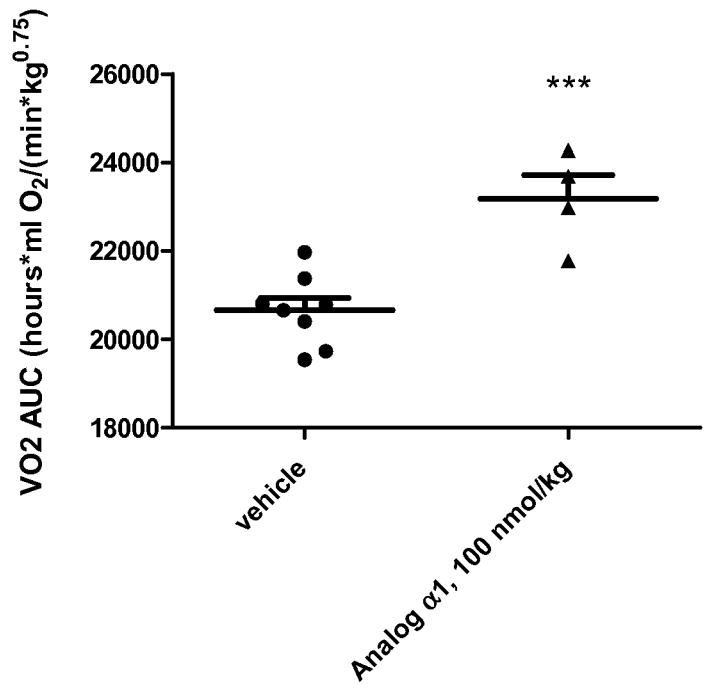
FIG. 7. Oxygen consumption ($VO_2$) expressed as AUC (Area Under Curve) over 24 hours in Diet Induced Obese (DIO) rats after acute treatment with Analog α1 (100 nmol/kg, s.c.) or vehicle (n=4-8). Data are means±SEM. (***p<0.001, t-test).

Based upon FIG. 7, it can be concluded that an analogue of alpha-CGRP causes increased energy expenditure in DIO rats.

Figure 8:
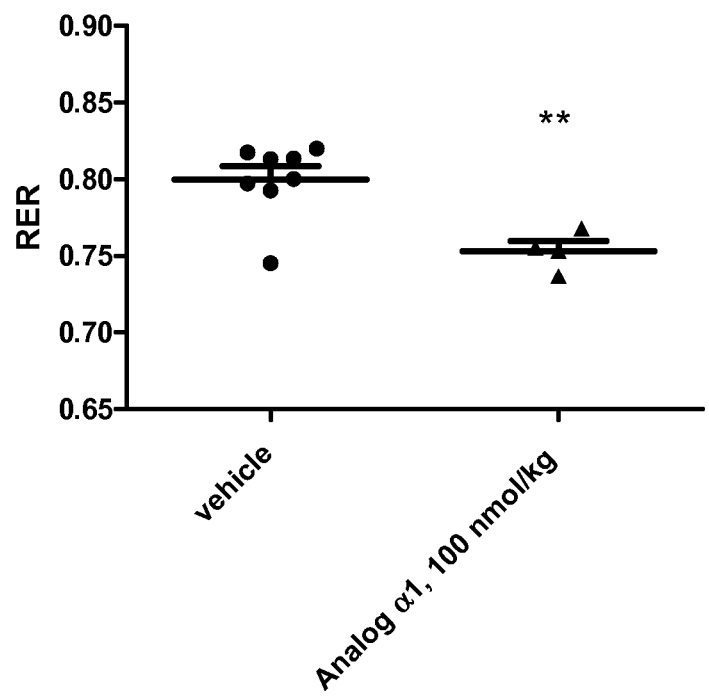
FIG. 8. Mean respiratory Exchange Ratio (RER) over 24 hours in DIO rats after acute treatment with Analog α1 (100 nmol/kg) or vehicle (n=4-8). Data are means±SEM. (**p<0.01, t-test).

Based upon FIG. 8, it can be concluded that an analogue of alpha-CGRP causes increased fat oxidation in DIO rat.

Figure 9:
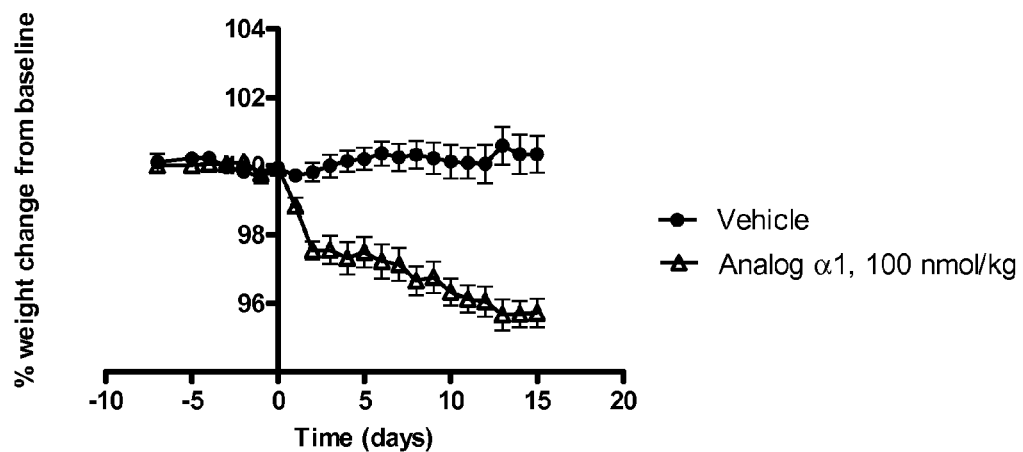
FIG. 9. Body weight change from baseline (%) in DIO rats after 14 days s.c. treatment with Analog α1 (100 nmol/kg) or vehicle. Data are means±SEM.

Based upon FIG. 9, it can be concluded that an analogue of alpha-CGRP causes weight loss in DIO rats.

Figure 10:
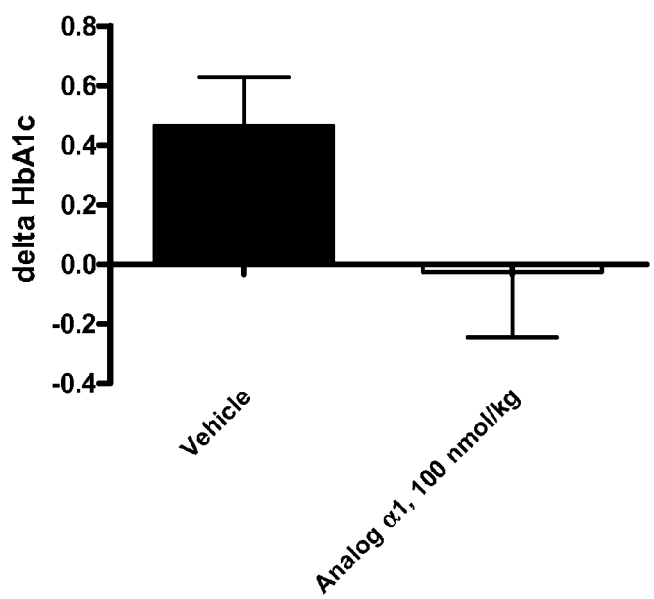
FIG. 10. Change in HbA1c in ob/ob mice after 14 days of treatment (s.c) with Analog a1 (100 nmol/kg) or vehicle. Data are means±SEM (p=0.09, t-test).
Figure 11:
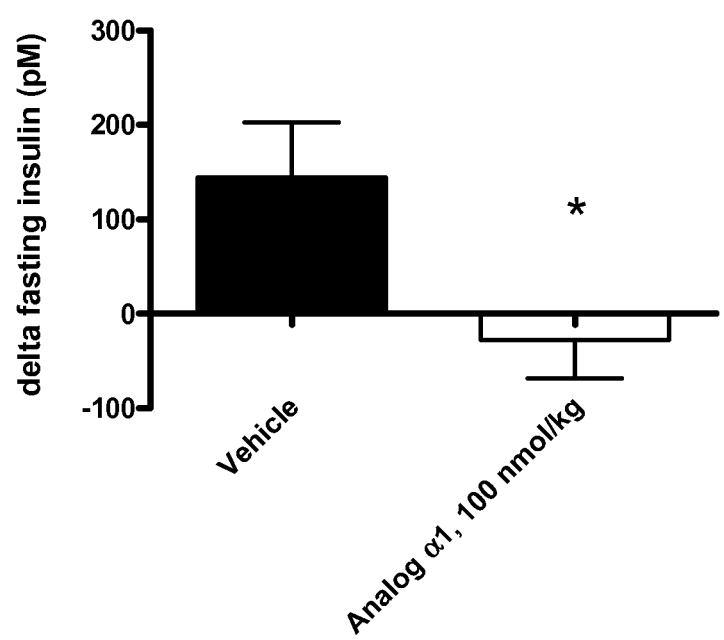
FIG. 11. Change in fasting plasma insulin in ob/ob mice after 14 days of treatment (s.c) with Analog α1 (100 nmol/kg) or vehicle. Data are means±SEM (*p<0.05, t-test).

Based upon FIG. 10, it can be concluded that an analogue of alpha-CGRP causes reduced levels of HbA1c in ob/ob mice Based upon FIG. 11, it can be concluded that an analogue of alpha-CGRP causes reduced levels of fasting insulin in ob/ob mice.

PREFERRED FEATURES OF THIS INVENTION

To sum up and supplement the above statements, the features of this invention are as follows:

1. Compounds of the general formula X—Y—Z, wherein X designates a CGRP compound from which, formally, a hydrogen has been removed from one of the amino groups present in an amino acid residue; Y is a linker as defined in claim 1 below; and Z is an acyl group; wherein the —Y—Z moiety is connected to an amino group present in an amino acid residue present in the CGRP compound.
2. A compound according to clause 1 wherein all the amino acid residues present in the CGRP compound can be coded for by the genetic triplet [i.e., is one of the essential amino acids].
3. A compound according to any one of the preceding clauses wherein the CGRP compound is CGRP-alpha.
4. A compound according to any one of the preceding clauses wherein the CGRP compound is CGRP-beta.
5. A compound according to any one of the preceding clauses wherein the CGRP compound is an analogue of CGRP-alpha.

6. A compound according to any one of the preceding clauses wherein the CGRP compound is an analogue of CGRP-beta.
7. A compound according to any one of the preceding clauses wherein the CGRP compound is a compound of formula I, more preferred a compound of formula II wherein exactly one of the amino acid residues is exchanged with another amino acid residue.
8. A compound according to any one of the preceding clauses wherein the CGRP compound is a compound of formula I, more preferred a compound of formula II, wherein exactly two of the amino acid residues is exchanged with another amino acid residue.
9. A compound according to any one of the preceding clauses wherein the CGRP compound is a compound of formula I, more preferred a compound of formula II, wherein exactly three of the amino acid residues is exchanged with another amino acid residue.
10. A compound according to any one of the preceding clauses wherein the CGRP compound is a compound of formula I, more preferred a compound of formula II, wherein exactly one amino acid residue is omitted.
11. A compound according to any one of the preceding clauses wherein the CGRP compound is a compound of formula I wherein a further amino acid residue is inserted.
12. A compound according to any one of the preceding clauses wherein the C terminal amino acid residue in the CGRP compound is Phe.
13. A compound according to any one of the preceding clauses wherein the C terminal amino acid residue in the CGRP compound is amidated phenylalanine, i.e., C$_6$H$_5$—CH$_2$—CH(—CONH$_2$)—NH— (wherein C$_6$H$_5$— is phenyl).
14. A compound according to any one of the preceding clauses wherein the CGRP compound has Ala or Ser in the 1 position.
15. A compound according to any one of the preceding clauses wherein the CGRP compound has Asn or Asp in the 3 position.
16. A compound according to any one of the preceding clauses wherein the CGRP compound has Met or Val in the 22 position.
17. A compound according to any one of the preceding clauses wherein the CGRP compound has Asn, Asp or Ser in the 25 position.
18. A compound according to any one of the preceding clauses wherein the CGRP compound has Glu or Lys in the 35 position.
19. A compound according to any one of the preceding clauses, to the extent possible, wherein the amino acid residues in positions 2, 4-21, 23, 24, 26-34, 36 and 37 of the CGRP compound has not been mutated [i.e., the amino acid residues in the specific positions mentioned in this clause are as mentioned in table 1 in Peptides loc cit.].
20. A compound according to any one of the preceding clauses, to the extent possible, wherein the amino acid residues in positions 2, 4-21, 23, 24, 26-34, 36 and 37 of the CGRP compound, except one of these amino acid residues, has not been mutated [i.e., the amino acid residues in the specific positions mentioned in this clause, except only one thereof, are as mentioned in table 1 in Peptides loc cit.].
21. A compound according to any one of the preceding clauses, to the extent possible, wherein the amino acid residues in positions 2, 4-21, 23, 24, 26-34, 36 and 37 of the CGRP compound, except two of these amino acid residues, has not been mutated [i.e., the amino acid residues in the specific positions mentioned in this clause, except two thereof, are as mentioned in table 1 in Peptides loc cit.].
22. A compound according to the preceding clause wherein the linker has the general formula:

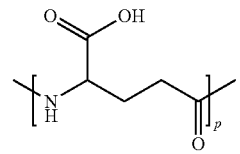

wherein p is an integer in the range from 1 through 23.
23. A compound according to the first of these clauses dealing only with the linker Y, wherein the linker has the general formula:

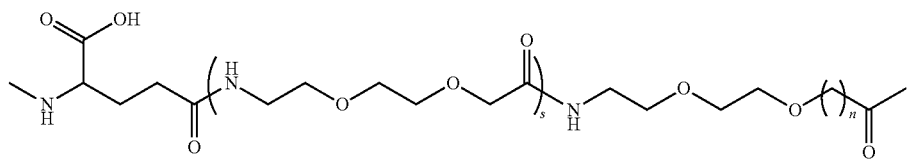

wherein n is 1, 2 or 3; and s is 0, 1, 2 or 3.
24. A compound according to the first of these clauses dealing only with the linker Y, wherein the linker has the general formula:

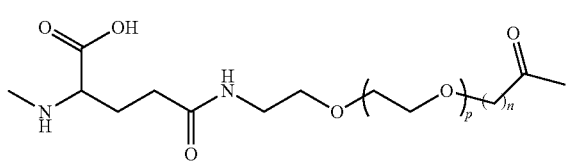

wherein n is 1, 2 or 3; and p is an integer in the range from 1 through 23.
25. A compound according to the first of these clauses dealing only with the linker Y, wherein the linker has the general formula:

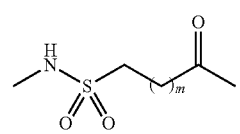

wherein m is zero or an integer in the range from 1 through 6.

26. A compound according to the first of these clauses dealing only with the linker Y, wherein the linker has the general formula:

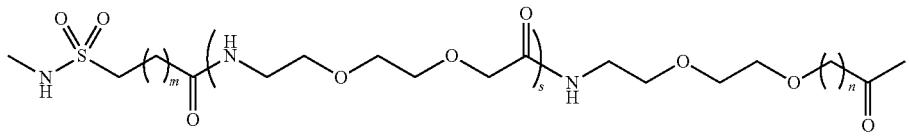

wherein m is zero or an integer in the range from 1 through 6; n is 1, 2 or 3; and s is 0, 1, 2 or 3.

27. A compound according to the first of these clauses dealing only with the linker Y, wherein the linker has the general formula:

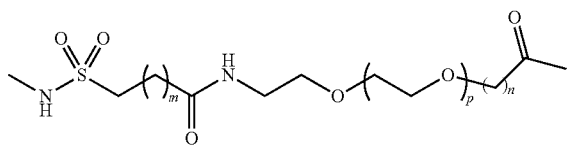

wherein m is zero or an integer in the range from 1 through 6; n is 1, 2 or 3; and p is an integer in the range from 1 through 23.

28. A compound according to any one of the preceding clauses, to the extent possible, wherein n in the linker designated Y is 1.

29. A compound according to any one of the preceding clauses, to the extent possible, wherein p in the linker designated Y is 1.

30. A compound according to any one of the preceding clauses, to the extent possible, wherein the linker is any one of the specific linkers present in the compounds mentioned in the above specific examples 1 et seq., preferably —NH—CH(COOH)—CH$_2$—CH$_2$—CO—NH—CH$_2$—CH$_2$—O—CH$_2$—CH$_2$—O—CH$_2$—CO—.

31. A compound according to any one of the preceding clauses, to the extent possible, wherein Z is an acyl group.

32. A compound according to the preceding clause, wherein the acyl group present in Z originates from a fatty acid or fatty diacid.

33. A compound according to the preceding clause, wherein the acyl group present in Z originates from a fatty diacid with an alpha and omega carboxy group.

34. A compound according to the preceding clause, wherein the acyl group present in Z originates from a fatty acid or fatty diacid with 12-22 carbon atoms.

35. A compound according to the preceding clause, wherein the acyl group present in Z originates from a fatty acid or fatty diacid with 16 carbon atoms.

36. A compound according to any one of the preceding clauses, to the extent possible, wherein the acyl group present in Z originates from a fatty acid or fatty diacid with 18 carbon atoms.

37. A compound according to any one of the preceding clauses, to the extent possible, wherein the acyl group present in Z originates from a fatty acid or fatty diacid with 20 carbon atoms.

38. A compound according to any one of the preceding clauses, wherein the moiety of the formula —Y—Z is connected to the CGRP compound at the N terminal amino acid residue [i.e., in position 1].

39. A compound according to the preceding clause, wherein the moiety of the formula —Y—Z is connected to the CGRP compound at the N terminal Ser.

40. A compound according to any one of the preceding clauses, to the extent possible, wherein the moiety of the formula —Y—Z is connected to the CGRP compound at a lysine residue.

41. A compound according to any one of the preceding clauses, to the extent possible, wherein the moiety of the formula —Y—Z is connected to the CGRP compound at Lys present in position 3.

42. A compound according to any one of the preceding clauses, to the extent possible, wherein the moiety of the formula —Y—Z is connected to the CGRP compound at Lys present in position 4.

43. A compound according to any one of the preceding clauses, to the extent possible, wherein the moiety of the formula —Y—Z is connected to the CGRP compound at Lys present in position 11.

44. A compound according to any one of the preceding clauses, to the extent possible, wherein the moiety of the formula —Y—Z is connected to the CGRP compound at Lys in position 24.

45. A compound according to any one of the preceding clauses, to the extent possible, wherein the moiety of the formula —Y—Z is connected to the CGRP compound at Lys present in position 25.

46. A compound according to any one of the preceding clauses, to the extent possible, wherein the moiety of the formula —Y—Z is connected to the CGRP compound at Lys present in position 26.

47. A compound according to any one of the preceding clauses, to the extent possible, wherein the moiety of the formula —Y—Z is connected to the CGRP compound at Lys present in position 28.

48. A compound according to any one of the preceding clauses, to the extent possible, wherein the moiety of the formula —Y—Z is connected to the CGRP compound at Lys present in position 29.

49. A compound according to any one of the preceding clauses, to the extent possible, wherein the moiety of the formula —Y—Z is connected to the CGRP compound at Lys present in position 31.

50. A compound according to any one of the preceding clauses, to the extent possible, wherein the moiety of the formula —Y—Z is connected to the CGRP compound at Lys in position 35.

51. A compound according to any one of the preceding product claims, which is any one of the compounds mentioned specifically in the above specification such as in the specific examples, especially any one of examples 1 et seq. below/above.

52. A compound according to any one of the preceding product claims for use as a medicament or for use in a medicament.

53. A compound according to any one of the preceding product claims for treating diabetes, insulin resistance, obesity, hypertension and cardiovascular disease.

54. The use of a compound according to any one of the preceding product claims for the preparation of a medicament for the treatment of diabetes, insulin resistance, obesity, hypertension and cardiovascular disease.
55. The use of a compound according to any one of the preceding product claims causing in vivo release of GLP-1.
56. The use of a compound according to any one of the preceding product claims causing weight reduction.
57. The use of a compound according to any one of the preceding product claims causing reduction in HbA1c level after prolonged exposure.
58. The use of a compound according to any one of the preceding product claims causing reduction in fasting insulin levels.
59. The use of a compound according to any one of the preceding product claims causing sustained vasodilatation.
60. The use of a compound according to any one of the preceding product claims causing increased energy expenditure.
61. A method of treatment of diabetes, insulin resistance, obesity, hypertension and cardiovascular disease, the method comprising administering to a subject in need thereof a therapeutically effective amount of a compound according to any one of the preceding product claims.
62. Any novel feature or combination of features described herein.

The following examples are offered by way of illustration, not by limitation.

The following abbreviations are used herein: Boc is t-butyloxycarbonyl, DCM is dichloromethane, Dde is 1-(4,4-dimethyl-2,6-dioxocyclohexylidene)ethyl, DIC is diisopropylcarbodiimide, DIPEA is diisopropylethylamine, Fmoc is 9-fluorenylmethyloxycarbonyl, h is hour(s), HATU is (O-(7-azabenzotriazol-1-yl)-1,1,3,3-tetramethyluronium hexafluorophosphate), HBTU is (2-(1H-benzotriazol-1-yl-)-1,1,3,3-tetramethyluronium hexafluorophosphate), HFIP is 1,1,1,3,3,3-hexafluoro-2-propanol or hexafluoroisopropanol, HOAt is 1-hydroxy-7-azabenzotriazole, HOBt is 1-hydroxybenzotriazole, HPLC is High Performance Liquid Chromatography, ivDde is 1-(4,4-dimethyl-2,6-dioxocyclohexylidene)-3-methylbutyl, LCMS is Liquid Chromatography Mass Spectroscopy, MeOH is methanol, Mmt is 4-methoxytrityl, Mtt is 4-methyltrityl, NMP is N-methylpyrrolidone, OEG is 8-amino-3,6-dioxaoctanic acid, OtBu is tert. butyl ester, PBS is Phosphate Buffered Saline, RP is Reverse Phase, RP-HPLC is Reverse Phase High Performance Liquid Chromatography, RT is Room Temperature, Rt is Retention time, SPPS is Solid Phase Peptide Synthesis, TFA is trifluoroacetic acid, TIPS is triisopropylsilane, TIS is triisopropylsilane, Trt is triphenylmethyl or trityl and HPLC is Ultra Performance Liquid Chromatography.

Methods of Preparation
General Methods

This section relates to methods for synthesising resin bound peptide (SPPS methods, including methods for de-protection of amino acids, methods for cleaving the peptide from the resin, and for its purification), as well as methods for detecting and characterising the resulting peptide (LCMS and HPLC methods).

Synthesis of Resin Bound Peptide
SPPS method A

SPPS method A refers to the synthesis of a protected peptidyl resin using Fmoc chemistry on an Applied Biosystems 433 peptide synthesizer (also designated ABI433A synthesizer) in 0.25 mmol or 1.0 mmol scale using the manufacturers FastMoc UV protocols which employ HBTU or HATU mediated couplings in NMP, and UV monitoring of the de-protection of the Fmoc protection group.

The starting resin used for the synthesis of peptide amides was a suitable Rink-Amide resin (for peptide amides), or (for peptides with a carboxy C-terminus) either a suitable Wang resin or a suitable chlorotrityl resin. Suitable resins are commercially available from, e.g., Novabiochem. The protected amino acid derivatives used were standard Fmoc-amino acids (supplied from e.g. Anaspec, or Novabiochem), in cartridges suitable for the ABI433A synthesizer. The N-terminal amino acid was Boc protected at the alpha amino group. If acylation of the N-terminal amino acid is desired the N-terminal amino acid was protected with Fmoc at the alpha amino group. The epsilon amino group of lysines in the sequence were either protected with Mtt, Mmt, Dde, ivDde, or Boc, depending on the route for attachment of the albumin binding moiety and spacer. The two cysteines in the sequence were protected with trityl groups that upon treatment with iodine in NMP cyclised to the desired disulphide bridged compound. The synthesis of the peptides may in some cases be improved by the use of di-peptides protected on the di-peptide amide bond with a group that can be cleaved under acidic conditions such as, but not limited to, 2-Fmoc-oxy-4-methoxybenzyl, or 2,4,6-trimethoxybenzyl. In cases where a serine or a threonine is present in the peptide, pseudoproline di-peptides may be used to improve the synthesis (available from, e.g., Novabiochem, see also W. R. Sampson (1999), J. Pep. Sci. 5, 403).

SPPS Method B

SPPS method B refers to peptide synthesis by Fmoc chemistry on a microwave-based Liberty peptide synthesizer (CEM Corp., North Carolina). A suitable resin is a pre-loaded, low-load Wang resin available from Novabiochem (e.g. low load fmoc-Lys(Mtt)-Wang resin, 0.35 mmol/g). Fmoc-deprotection was with 5% piperidine in NMP at up to 70 or 75° C. The coupling chemistry was DIC/HOAt in NMP. Amino acid/HOAt solutions (0.3 M in NMP at a molar excess of 3-10 fold) were added to the resin followed by the same molar equivalent of DIC (0.75M in NMP). For example, the following amounts of 0.3M amino acid/HOAt solution were used per coupling for the following scale reactions: Scale/ml, 0.10 mmol/2.5 ml, 0.25 mmol/5 ml, 1 mmol/15 ml. Coupling times and temperatures were generally 5 minutes at up to 70 or 75° C. Histidine amino acids were double coupled at 50° C., or quadruple coupled if the previous amino acid was sterically hindered (e.g. Aib). Arginine amino acids were coupled at RT for 25 min then heated to 70 or 75° C. for 5 min. For protection of the N-terminal amino acid and the epsilon amino group of lysines, please refer to SPPC method A, above. The Mtt group was removed by washing the resin with DCM and suspending the resin in neat (undiluted) hexafluoroisopropanol for 20 minutes followed by washing with DCM and NMP. The chemical modification of the lysine was performed either by manual synthesis or by one or more automated steps on the Liberty, optionally including a manual coupling.

Procedure for De-Protection
Removal of ivDde or Dde-Protection

The resin (0.25 mmol) was placed in a manual shaker/filtration apparatus and treated with 2% hydrazine in N-methylpyrrolidone (20 ml, 2×12 min) to remove the Dde or ivDde group and wash with N-methylpyrrolidone (4×20 ml).

Removal of Mtt or Mmt-Protection

The resin (0.25 mmol) was placed in a manual shaker/filtration apparatus and treated with 2% TFA and 2-3% TIS in DCM (20 ml, 5-10 min repeated 6-12 times) to remove the Mtt or Mmt group and wash with DCM (2×20 ml), 10% MeOH and 5% DIPEA in DCM (2×20 ml) and N-methylpyrrolidone (4×20 ml).

Formation of Disulphide Bridge

The protected resin (0.25 mmol) was placed in a manual shaker/filtration apparatus and washed with NMP before a solution of iodine (635 mg, 2.5 mmol) in NMP (10 mL) was added. The mixture was agitated for 30 min before it was drained and washed with NMP (3×10 mL). A solution of ascorbic acid (441 mg, 2.5 mmol) in NNP-water (9:1, 10 mL) was added and the mixture was agitated for 15 min before the mixture was drained and washed with NMP (10×10 mL) and DCM (10×10 mL).

Cleavage from the Resin

After synthesis the resin was washed with DCM, and the peptide was cleaved from the resin by a 2-3 hour treatment with TFA/TIS/water (95/2.5/2.5 or 92.5/5/2.5) followed by precipitation with diethylether.

Purification and Quantification

The crude peptide is dissolved in a suitable mixture of water and MeCN or methylformamide and purified by reversed-phase preparative HPLC (Waters Deltaprep 4000 or Gilson) on a column containing C18-silica gel. Elution is performed with an increasing gradient of MeCN in water containing 0.1% TFA. Relevant fractions are checked by analytical HPLC or HPLC. Fractions containing the pure target peptide are mixed and concentrated under reduced pressure. The resulting solution is analyzed (HPLC, LCMS) and the product is quantified using a chemiluminescent nitrogen specific HPLC detector (Antek 8060 HPLC-CLND) or by measuring UV-absorption at 280 nm. The product is dispensed into glass vials. The vials are capped with Millipore glassfibre prefilters. Freeze-drying for three days affords the peptide trifluoroacetate as a white solid.

Methods for Detection and Characterization

LCMS Methods

LCMS

LCMS was performed on a setup consisting of Waters Acquity HPLC system and LCT Premier XE mass spectrometer from Micromass. The HPLC pump was connected to two eluent reservoirs containing:

A: 0.1% formic acid in water.
B: 0.1% formic acid in acetonitrile.

The analysis was performed at RT by injecting an appropriate volume of the sample (preferably 2-10 µl) onto the column which was eluted with a gradient of A and B.

The UPLC conditions, detector settings and mass spectrometer settings were:

Column: Waters Acquity HPLC BEH, C-18, 1.7 µm, 2.1 mm×50 mm.
Gradient: Linear 5%-95% acetonitrile during 4.0 min (alternatively 8.0 min) at 0.4 ml/min.
Detection: 214 nm (analogue output from TUV (Tunable UV detector)).
MS ionisation mode: API-ES.
Scan: 100-2000 amu (alternatively 500-2000 amu), step 0.1 amu.

HPLC Methods

Method 05_B5_1

HPLC (method 05_B5_1): The RP-analysis was performed using a Waters HPLC system fitted with a dual band detector. UV detections at 214 nm and 254 nm were collected using an ACQUITY HPLC BEH130, C18, 130 Å, 1.7 um, 2.1 mm×150 mm column, 40° C.

The HPLC system was connected to two eluent reservoirs containing:

A: 0.2 M $Na_2SO_4$, 0.04 M $H_3PO_4$, 10% $CH_3CN$ (pH 3.5).
B: 70% $CH_3CN$, 30% $H_2O$.

The following linear gradient was used: 60% A, 40% B to 30% A, 70% B over 8 minutes at a flow-rate of 0.40 ml/min.

Method 04_A3_1

HPLC (method 04_A3_1): The RP-analysis was performed using a Waters HPLC system fitted with a dual band detector. UV detections at 214 nm and 254 nm were collected using an ACQUITY HPLC BEH130, C18, 130 Å, 1.7 um, 2.1 mm×150 mm column, 40° C.

The HPLC system was connected to two eluent reservoirs containing:

A: 90% $H_2O$, 10% $CH_3CN$, 0.25 M ammonium bicarbonate.
B: 70% $CH_3CN$, 30% $H_2O$.

The following linear gradient was used: 75% A, 25% B to 45% A, 55% B over 16 minutes at a flow-rate of 0.40 ml/min.

Method 04_A4_1

HPLC (method 04_A4_1): The RP-analysis was performed using a Waters HPLC system fitted with a dual band detector. UV detections at 214 nm and 254 nm were collected using an ACQUITY HPLC BEH130, C18, 130 Å, 1.7 um, 2.1 mm×150 mm column, 40° C.

The HPLC system was connected to two eluent reservoirs containing:

A: 90% $H_2O$, 10% $CH_3CN$, 0.25 M ammonium bicarbonate.
B: 70% $CH_3CN$, 30% $H_2O$.

The following linear gradient was used: 65% A, 35% B to 25% A, 65% B over 16 minutes at a flow-rate of 0.40 ml/min.

Method 08_B2_1

HPLC (method 08_B2_1): The RP-analysis was performed using a Waters HPLC system fitted with a dual band detector. UV detections at 214 nm and 254 nm were collected using an ACQUITY HPLC BEH130, C18, 130 Å, 1.7 um, 2.1 mm×150 mm column, 40° C.

The HPLC system was connected to two eluent reservoirs containing:

A: 99.95% $H_2O$, 0.05% TFA.
B: 99.95% $CH_3CN$, 0.05% TFA.

The following linear gradient was used: 95% A, 5% B to 40% A, 60% B over 16 minutes at a flow-rate of 0.40 ml/min.

Method 08_B4_1

HPLC (method 08_B4_1): The RP-analysis was performed using a Waters HPLC system fitted with a dual band detector. UV detections at 214 nm and 254 nm were collected using an ACQUITY HPLC BEH130, C18, 130 Å, 1.7 um, 2.1 mm×150 mm column, 40° C.

The HPLC system was connected to two eluent reservoirs containing:

A: 99.95% $H_2O$, 0.05% TFA.
B: 99.95% $CH_3CN$, 0.05% TFA.

The following linear gradient was used: 95% A, 5% B to 95% A, 5% B over 16 minutes at a flow-rate of 0.40 ml/min.

The following linear gradient was used: 40% A, 60% B to 20% A, 80% B over 8 minutes at a flow-rate of 0.40 ml/min.

Example 1

N-alpha-[2-(2-{2-[(S)-4-Carboxy-4-(17-carboxyheptadecanoylamino)butyrylamino]ethoxy}ethoxy)acetyl][Ser1]alpha-human CGRP peptide

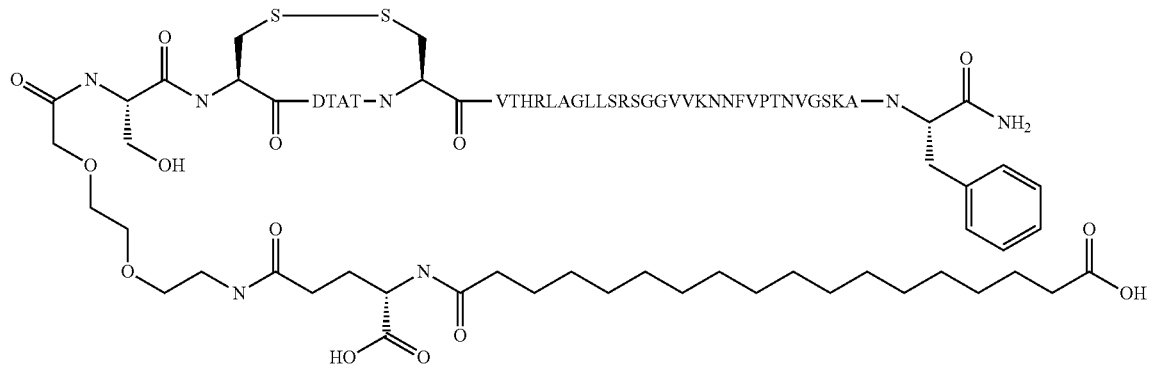

Preparation: SPPS method A, starting with H-PAL HMPB-ChemMatrix resin (loading 0.43 mmol/g, 0.582 g, 0.25 mmol). The following pseudo prolines employed are available from Novabiochem; Fmoc-Leu-Ser($\psi^{Me,Me}$pro)-OH and Fmoc-Val-Thr($\psi^{Me,Me}$pro)-OH. Building block 8-(9-fluorenylmethyloxycarbonylamino)-3,6-dioxaoctanoic acid are commercially available from Iris Biotech and octadecanedioic acid mono tert-butyl ester was prepared as described in WO 2005/012347.

HPLC 08_B2__1: 11.90 min.
HPLC 08_B4__1: 7.88 min.
HPLC 04_A4__1: 10.16 min.
LCMS: m/z=1459.2 $(M+3H)^{3+}$, 1094.5 $(M+4H)^{4+}$, 875.6 $(M+5H)^{5+}$

Example 2

N-alpha-[2-(2-{2-[(S)-4-Carboxy-4-(17-carboxyheptadecanoylamino)butyrylamino]ethoxy}ethoxy)acetyl][Ser1]beta-human CGRP peptide

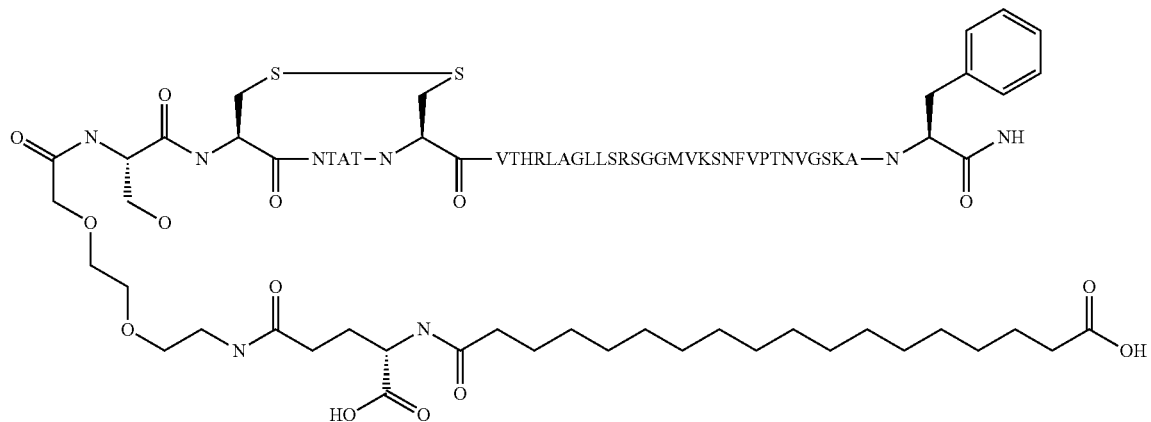

Preparation: SPPS method B starting with ChemMatrix Rink Amide resin (0.25 mmol). The following amino acids were double coupled; glycine (position 20) and glycine (position 14). Building block 8-(9-fluorenylmethyloxycarbonylamino)-3,6-dioxaoctanoic acid are commercially available from Iris Biotech and octadecanedioic acid mono tert-butyl ester was prepared as described in WO 2005/012347.

HPLC 08_B4_1: 8.31 min.
HPLC 04_A3_1: 13.52 min.
LCMS: m/z=1461.1 (M+3H)$^{3+}$, 1096.3 (M+4H)$^{4+}$ Example 3

N-alpha-[2-(2-{2-[(S)-4-Carboxy-4-(17-carboxyheptadecanoylamino)butyrylamino]ethoxy}ethoxy)acetyl]alpha-human CGRP peptide

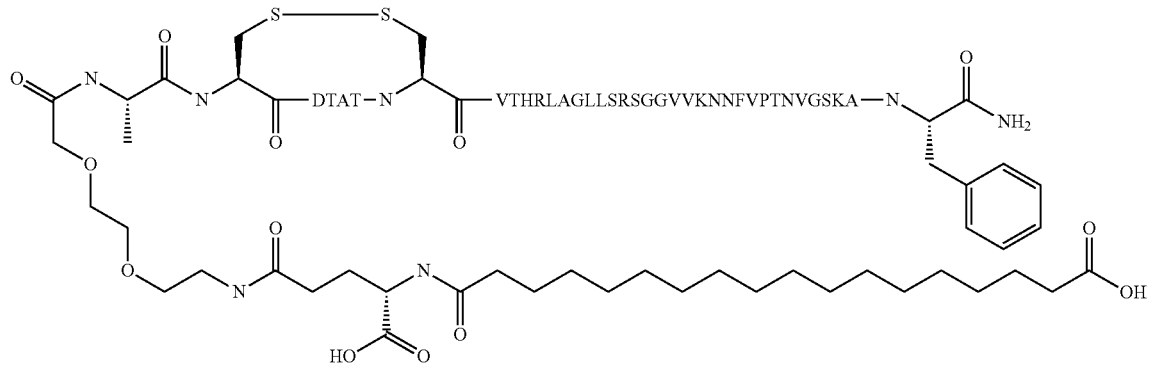

Preparation: SPPS method A, starting with H-PAL HMPB-ChemMatrix resin (loading 0.43 mmol/g, 0.582 g, 0.25 mmol). The following pseudo prolines employed are available from Novabiochem; Fmoc-Leu-Ser($\psi^{Me,Me}$pro)-OH and Fmoc-Val-Thr($\psi^{Me,Me}$pro)-OH. Building block 8-(9-fluorenylmethyloxycarbonylamino)-3,6-dioxaoctanoic acid are commercially available from Iris Biotech and octadecanedioic acid mono tert-butyl ester was prepared as described in WO 2005/012347.

HPLC 08_B4_1: 8.21 min.
HPLC 08_B2_1: 12.39 min.
HPLC 05_B5_1: 5.15 min.
HPLC 04_A3_1: 13.27 min.
LCMS: m/z=1453.69 (M+3H)$^{3+}$, 1090.50 (M+4H)$^{4+}$, 872.42 (M+5)$^{5+}$ Example 4

In table 1 below, is given pharmacokinetic parameters ($EC_{50}$, $C_{max}$ and T½) and in vitro potencies of two known compounds, i.e., rat CGRP-alpha and rat CGRP-beta, and of two compounds of this invention, i.e., the compounds mentioned specifically in example 1 and 2, above.

TABLE 1

|  | CGRP-alpha | CGRP-beta | Analogue alpha 1 | Analogue beta 1 |
|---|---|---|---|---|
| $EC_{50}$, pM | 5 | 9 | 90 | 12 |
| $C_{max}$, nM |  |  | 250 | 210 |
| T½, hours |  |  | >7 | >7 |

It appears from the data in table 1, that potent acylated CGRP analogues with Cmax>200 times that of native peptides (i.e. CGRP) and with T½>7 h have been produced. These peptides allow the identification of novel biological activities and determining the net effect of many metabolic effects of CGRP.

Examples 5-13

Background

Certain acylation positions (meaning substitution of an amino acid in human alpha CGRP by N-ε-{2-(2-{2-[2-(2-{2-[4-carboxy-4-(17-carboxyheptadecanoylamino)butyrylamino]ethoxy}ethoxy)acetylamino]-ethoxy}ethoxy)acetyl})-L-lysine or N-terminal acylation with {2-(2-{2-[2-(2-{2-[4-carboxy-4-(17-carboxyheptadecanoylamino)butyrylamino]ethoxy}ethoxy)acetylamino]ethoxy}ethoxy) acetyl} in human alpha CGRP) were evaluated in the in vitro assay (CGRP-induced cAMP accumulation in CGRP receptor expressing cells) using high-throughput peptide synthesis on cellulose paper (SPOT synthesis, see *J. Immunol. Methods.* 2002 Sep. 1; 267(1):13-26. The SPOT-synthesis technique. Synthetic peptide arrays on membrane supports—principles and applications. Frank R.) via a photo cleavable linker yielding soluble peptides ready for assaying.

Synthesis of Cellulose Bound Peptides

The peptides were synthesized in double (two copies) on standard amino-modified acid stable cellulose membrane with PEG-Spacer from AIMS Scientific Products GmbH (Germany) in 96-well format using a fully automated Multi-Pep robot from Intavis Bioanalytical Instruments (Germany) equipped with the AutoSpot module. Couplings were performed in triple using HOAt/DIPCDI/collidine preactivation (0.4 µl 1 M DIC in NMP, 0.2 µl 1 M collidine in NMP, 0.3 M Fmoc amino acid in 0.3 M HOAt in NMP per SPOT for 30 min). Fmoc deprotection was performed by treating each membrane with 20% piperdine in NMP (2×6 ml) for 10 min. Membrane washing was with NMP (6×6 ml) and EtOH (6×6 ml) via the robot manifold followed by drying. The membrane was first derivatized with Fmoc-Gly-OH/Boc-Gly-OH (1:1) followed by capping with NMP/AcO2/DIPEA (94:5:1) (SPOT definition and membrane loading adjustment) and washing. After Fmoc removal, coupling of Fmoc-Photo-Linker (RL-1026, available from Iris Biotech GmbH), and washing, the peptides were synthesized using the repetitive cycle of deprotection, coupling and washing stated above. When an acylation was present on a lysine sidechain the epsilon amino group of lysine to be acylated was protected with Mtt (e.g. Fmoc-Lys(Mtt)-OH) and the N-terminal alpha amino group was protected with Boc (e.g. Boc-Ala-OH). When the peptide backbone sequence was completed the membrane was treated with HFIP/DCM (75:25, 3×20 ml) for 10 min followed by positive bromophenolblue test. The acylation group was then introduced using the repetitive cycle of deprotection, coupling and washing. The following building blocks were used Fmoc-OEG-OH, Fmoc-Glu-OtBu, and C18diacid mono tert-butyl ester. The cellulose sheet was dried, placed in a polypropylene tray, washed with NMP before a solution of iodine (635 mg, 2.5 mmol) in NMP (10 mL) was added. The sheet was agitated for 30 min before the mixture was decanted and the sheet washed with NMP (3×10 mL). A solution of ascorbic acid (441 mg, 2.5 mmol) in NNP-water (9:1, 10 mL) was added and the sheet was agitated for 15 min before the mixture was decanted and the sheet washed with DCM (5×20 ml), NMP (5×20 ml), and EtOH (5×20 ml).

Cleavage of Celloluse Bound Peptides

After synthesis the cellulose membrane was washed with DCM (5×20 ml), dried, and the sidechain protection groups were removed by a 2 hour treatment with TFA/TIPS/water (92.5/5.0/2.5) followed by washings with DCM (5×20 ml), NMP (5×20 ml), and EtOH (5×20 ml). The dried membrane was placed on a transilluminator irradiating at 365 nm for 3 hrs. The SPOT were punched out and placed in a filtration 96-well miroplate. 40 µl DMSO was added to each SPOT and the plate was shaken for 30 min. The filtrate from each well was collected and 160 µl HBSS 1× with 20 mM Hepes, 0.1% ovalbumin, 0.005% Tween20 was added to each well yielding the crude peptides in solution ready for assaying the CGRP-induced cAMP accumulation in CGRP receptor expressing cells.

The test results obtained are given in Table 2.

TABLE 2

| Acylation Position | pEC$_{50}$-ratio relative to human alpha-CGRP, measured by the CGRP-induced cAMP accumulation in CGRP receptor expressing cells |
|---|---|
| None* | 1.00 |
| 28 | 0.62 |
| 31 | 0.44 |
| 29 | 0.41 |
| 26 | 0.38 |
| 11 | 0.28 |
| 24 | 0.28 |
| 25 | 0.23 |
| 4 | 0.15 |
| 3 | 0.14 |

*= native human alpha-CGRP

The data in Table 2 shows the acylation scan with N-ε-{2-(2-{2-[2-(2-{2-[4-carboxy-4-(17-carboxyheptadecanoylamino)butyrylamino]ethoxy}ethoxy)acetylamino]ethoxy}ethoxy)acetyl})-L-lysine of human alpha-CGRP prepared as individual SPOTs in double on cellulose sheet functionalized with a photo cleavable linker, cleaved from cellulose with UV light at 365 nm, solubilized in DMSO and assayed in CGRP-1-luc cell line receptor assay.

The following table indicates which compounds were tested in Table 2. The column with the heading indicates in which position in the CGRP compound the side chain was attached.

| Peptide No | Cys2 and Cys7 are cyclised with a disulfide bond |
|---|---|
| CGRP | A-C-D-T-A-T-C-V-T-H-R-L-A-G-L-L-S-R-S-G-G-V-V-K-N-N-F-V-P-T-N-V-G-S-K-A-F |
| 3 | A-C-X-T-A-T-C-V-T-H-R-L-A-G-L-L-S-R-S-G-G-V-V-K-N-N-F-V-P-T-N-V-G-S-K-A-F |
| 4 | A-C-D-X-A-T-C-V-T-H-R-L-A-G-L-L-S-R-S-G-G-V-V-K-N-N-F-V-P-T-N-V-G-S-K-A-F |
| 11 | A-C-D-T-A-T-C-V-T-H-X-L-A-G-L-L-S-R-S-G-G-V-V-K-N-N-F-V-P-T-N-V-G-S-K-A-F |
| 24 | A-C-D-T-A-T-C-V-T-H-R-L-A-G-L-L-S-R-S-G-G-V-V-X-N-N-F-V-P-T-N-V-G-S-K-A-F |
| 25 | A-C-D-T-A-T-C-V-T-H-R-L-A-G-L-L-S-R-S-G-G-V-V-K-X-N-F-V-P-T-N-V-G-S-K-A-F |
| 26 | A-C-D-T-A-T-C-V-T-H-R-L-A-G-L-L-S-R-S-G-G-V-V-K-N-X-F-V-P-T-N-V-G-S-K-A-F |
| 28 | A-C-D-T-A-T-C-V-T-H-R-L-A-G-L-L-S-R-S-G-G-V-V-K-N-N-F-X-P-T-N-V-G-S-K-A-F |
| 29 | A-C-D-T-A-T-C-V-T-H-R-L-A-G-L-L-S-R-S-G-G-V-V-K-N-N-F-V-X-T-N-V-G-S-K-A-F |
| 31 | A-C-D-T-A-T-C-V-T-H-R-L-A-G-L-L-S-R-S-G-G-V-V-K-N-N-F-V-P-T-X-V-G-S-K-A-F |

X = N-ε-{2-(2-{2-[2-(2-{2-[4-carboxy-4-(17-carboxyheptadecanoylamino)butyrylamino]ethoxy}ethoxy)-acetylamino]ethoxy}ethoxy)acetyl})-L-lysine Methods of Biological Evaluation CGRP-Induced cAMP Accumulation in CGRP Receptor Expressing Cells Chinese hamster ovary (CHO) cells were stably transfected with calcitonin receptor-like receptor (CRLR), receptor activity modifying protein-1 (RAMP1) and CRE luciferase (cAMP responsive element for control of luciferase gene expression). Luciferase is a reporter-gene reporting accumulation of intracellular cAMP).

Cells were cultured in F12 media supplemented with GlutaMAX™ (Gibco cat no 31765-027), FBS (10%, Gibco 16140-071), Penicillin-streptomycin (1%, Lonza DE-17-602E), G418 (400 µg/ml, Gibco 10131-027), Blasticidine (10 µg/ml, Corning cat no 15205), Hygromycin (400 µg/ml, Calbiochem cat no 400052).

Cells were seeded in a 96 well plate (Packard #6005180), 20000 cells/well in 100 µl media on the day before experimentation. On the day of experimentation media was replaced by assay medium (Dulbecco's media w/o phenol red (Gibco cat no 11880-028) supplemented with 10% FBS (10%, Gibco 16140-071), Hepes (10 mM, Gibco cat no 15630), GlutaMAX™ (2 mM, Gibco cat no 35050), 50 µl/well.

Peptides were diluted in assay media before added to cells for stimulation, 50 µl/well.

Cells were incubated 5% CO$_2$, 37° C. for 4 hours.

Assay medium and peptides were replaced by phosphate buffered saline (PBS, Gibco cat no 14040-091), 100 µl/well and LucLite™ (PerkinElmer, cat no 6076759), 100 µl/well were added. The plate was sealed before incubation for 30 min at room temperature (21° C.). Luciferase activity (luminescens, 7 s/well) was measured (TopCount®, NXT, Packard).

Dose-response curves were fitted by use of GraphPad Prism software and pEC$_{50}$ values were calculated. Data were given as mean±SEM, n=2 and each analogue was tested twice.

CGRP-Induced GLP-1 Release in Gut L-Cell Line

The murine intestinal L-cell line, GLUTag were grown in DMEM (Gibco cat no 21885-010) supplemented with FCS (10%, Gibco) and Penicillin-streptomycin (1%, Gibco cat no 15140-114).

Cells were seeded in 96 well plates (Biological Industries, cat no E-TCMT-F), 50.000 cells/well in 200 µl media and cultured over night. Cells were stimulated for 3 hours at 37° C. with CGRP, analogues or controls in assay medium containing DMEM (Gibco 21885-010) supplemented with BSA (0.1%, Sigma cat no A4503), Tween20 (0.005%, Merck, cat no 822184) and valpyr (200 µM)). Media were collected and immediately stored at −20° C. until analysis of GLP-1 content as described below (Measurement of total GLP-1 in plasma and media). Data was analysed using GraphPad Prism and results given as mean±SEM. All analogues have been tested in duplicate with n=2.

CGRP-Induced Reduction in Food Intake by Automatic Food Intake Measurements (FeedWin)

Upon arrival male Sprague Dawley (SD) rats were housed two per cage with a dividing wall between them. They were housed at reversed diurnal rhythm and with environmental enrichment. The rats were acclimatized to reversed diurnal rhythm for at least 1 week before being transferred to the experimental system cages (single housed). They were acclimatized to the experimental system cages for an additional 5-6 days before start of the experiment. The rats had ad libitum access to food (Altromin 1324) and water during acclimatization periods.

One day before start of the study the rats were divided in three or four groups (n=5-8) based on body weight (250-300 g).

16 hours before start of the study the rats were fasted. Food was returned in connection with dosing. The rats received a single injection subcutaneously (s.c., 1 ml/kg) with vehicle or CGRP analogue. Intraperitoneally dosing (i.p., 1 ml/kg) was used in the first experiment of the a1 analogue. The effect of analogues on food and water consumption was examined in a "FeedWIN" system (Ellegaard Systems A/S, Faaborg, Denmark). The system contained 32 stations. In each station the continuous water and food consumption for a single rat was recorded.

A station consisted of a cage with metal lid and two scales placed on each side of the cage. The scales registered weight removed from food and water containers and thus the individual consumption of food and water respectively. The 32 stations were connected with two PC's that collected and processed data via a specially designed software (FeedWIN). Data was collected each 15 minutes and up to 48 hours and expressed as accumulated food intake (Mean±SEM).

Pharmacokinetic and GLP-1-Release Properties of CGRP and Analogues Thereof.

Male Sprague Dawley rats (n=24) weighing approximately 250 g were used for the combined pharmacokinetic (T½, Cmaxetc.) and pharmacodynamic (GLP-1 release) study. The rats were divided in 4 groups with n=6 rats per group. The rats were treated with a single subcutaneous injection (1 ml/kg) of vehicle, alpha-CGRP (138 nmol/kg), Analogue beta1 (231 nmol/kg) or Analog alpha1 (151 nmol/kg). Blood (200 µl) was sampled from vena sublingualis from unanaesthetised rats pre-dose and at 0.5, 1, 3, 7 and 24 hours post dosing. Blood was collected in tubes containing EDTA. The samples were kept on ice and centrifuged. The plasma was kept at −20° C. until analysis for CGRP analog and total GLP-1.

A commercial available kit (Human CGRP ELISA, cat. #A05481, SPIbio) was used for monitoring the plasma levels of CGRP-analogues. Briefly, the assay was a two-sited enzyme-linked immuno sorbent assay (ELISA) using two antibodies against human CGRP. A monoclonal antibody was immobilized to the surface of micro plate wells. Five micro liter of plasma samples or calibrators were applied to the appropriate wells and incubated for 2 hours together with 100 µL buffer and 100 µL AChE-conjugated Fab' fragment. The wells were then emptied, washed and Ellman's Reagent was added to each well and incubated for additional 30-90 minutes in dark. The color intensity was determined by spectrophotometer at 405 nm. The level of signal was proportional to the concentration of CGRP-analogue in the plasma samples. CGRP-analogues was diluted in plasma (Bioreclamation, UK) and used as calibrators. A line of calibrators were prepared covering a range from 0 to 30000 pM. The calibrators were stored in Micronic tubes at −18° C. The lower limit of quantification of the modified CGRP assay was approximately 750 pM and the imprecision was (% CV)<10%.

Measurement of Total GLP-1 in Plasma and Media

Plasma or cell media samples were analyzed for the level of total GLP-1 using Luminescence Oxygen Channeling Immunoassay (LOCI). Two micro liters of calibrator, control and unknown plasma samples were pipetted into the wells of grey 384-well micro titer plates (Perkin Elmer) followed by 15 µL mixture of acceptor beads (0.5 µg/well) coated with mAbF5 (Pridal L, Ingwersen S H, Larsen F S, Hoist J J, Adelhorst K, Kirk O. Comparison Of Sandwich-Linked Immunoabsorbent Assay Radioimmunoassay For Determination Of Exogenous Glucagon-Like Peptide-1(7-36)Amide In Plasma. *J Pharm Biomed. Anal.* 1995, 13:841-50) and biotinylated HYP147-12 (AntibodyShop, DK) (4 nmol/L). The plates were incubated for 1 hr at 18-22° C. Then 30 µL streptavidin-coated donor-beads (2 µg/well) (Perkin Elmer) were added to each well and incubated for 30 minutes at 21-22° C. The plates were red in an Envision plate reader (Perkin Elmer) at 21-22° C. with a filter having a bandwidth of 520-645 nm after excitation by a 680 nm laser. The total measurement time per well was 210 ms including a 70 ms excitation time. Human GLP-1 (Novo Nordisk) was diluted in a HEPES-buffered solution and used as calibrator. A line of calibrators was prepared covering a range from 2 to 2000 pmol/L. The calibrators were stored in Micronic tube at −18° C. The detection limit defined as the concentration corresponding to 3 SD above the mean of 21 determinations of the zero calibrator, was 1.0 pmol/L and the imprecision (CV) was assessed by the measurement of three samples in 12 consecutive analytical runs and 21 determinations of each of the three samples in the same analytical run; the overall CV was <10%.

Continuous Detection of Blood Pressure

Seven female Sprague Dawley (SD) rats, approximately 9 months old at delivery (Taconic M&B), were all pair housed with partner rats in super-enriched cages and included in the study. The rats were in the weight range of 301-424 gram at start of the study. Before inclusion in the study, the rats were after an acclimatisation period of at least 2 to 3 weeks in the animal house anaesthetised with Isoflurane (Baxter A/S, Allerød, Denmark) and intra-peritoneally implanted with a TL11M2-C50-PXT telemetry transmitter (Data Sciences International (DSI), St. Paul, US) and an arterial catheter was placed in the femoral artery and tunnelled into the aorta for arterial blood pressure measurements. Pre-emptively, they received 0.05-0.1 mg/kg buprenorphin (Temgesic, Schering-Ploug A/S, Farum, Denmark) and 5 mg/kg Rimadyl Vet. (Orion Pharma, Nivå, Denmark) as analgesia plus 0.05 ml/100 g Streptocillin Vet. 2000.000 IE (Boehringer Ingelheim, København Ø, Denmark) as prophylactic antibiotic treatment. For the following two days they received 5 mg/kg Rimadyl Vet. (OrionPharma, Nivå, Denmark) as post-operative analgesia. All rats were allowed a restitution period of at least four weeks post-operatively and had to pass a general health check before taking part in the study. The data acquisition program Notocord-HEM v. 3.5 (Notocord, Croissy Sur Seine, France) was used to acquire and display the haemodynamic signals obtained by telemetry. All rats had their blood pressure and heart rate monitored for up to 24 hours.

Mean arterial blood pressure (systolic and diastolic blood pressure were also monitored) was evaluated as mean values at pre-dose (t=0) and up to 24 hours after dosing (high doses only).

Measurement of Oxygen Consumption ($VO_2$) and Respiratory Exchange Ratio (RER)

Eight male Sprague Dawley OBESE Prone rats (Charles River) were used for the study. They were group housed in normal diurnal rhythm and had ad libitum access to high fat diet (60 kcal % from fat, R12492) and water. The rats have been fed high fat diet for 11 weeks when tested for energy expenditure.

The effect of the compounds to be tested on energy expenditure was determined in an Oxy-max System 2 (Columbus Instrument—Open Circuit calorimeter version 2.30) by indirect calorimetry from respiratory gas exchange. The animals were weighed and placed individually in a respiration chamber with constant ventilation. Air was pulled in at a constant rate (1.8 l/min) and flow out was 0.8 l/min. The $O_2$ consumption and $CO_2$ production of the animal are measured at a sampling interval of 9 minutes.

After two hours acclimatization the rats were dosed s.c. with Analog α1 (100 nmol/kg) or vehicle (cross over design). Data was collected for 22 hours and converted into $VO_2$ and respiratory exchange ratio (RER).

The results obtained are shown in FIG. 7 and FIG. 8.

Food Intake and Body Weight After Subchronic Administration in DIO Rats

Eighteen Sprague Dawley rats were used for the study. When starting the study the rats were approximately 1 year old and had been on high fat diet (Research Diet, D12451 45%) for 10 months. 14 days before study start they were singlehoused and had ad libitum access to food and water. They were treated once daily with Analog α1 (100 nmol/kg, s.c.) or vehicle for 14 days.

Body weight was measured once daily.

The results obtained are shown in FIG. 9.

Blood Glucose, Plasma Insulin and HbA1c After Subchronic Administration in ob/ob Mice Twenty male UMEÅ ob/ob mice (Taconic, Denmark) were used for the study. The mice were housed in regular diurnal rhythm and had ad libitum access to regular chow and water. At study start they were 8 weeks old. Before starting the study, blood samples for HbA1c were taken. Basal blood samples were also taken after overnight semi fasting for measurement of fasting insulin. The mice were dosed s.c. once daily with 100 nmol/kg of Analog α1 or vehicle. The study commenced for 14 days. At the end of study blood samples were again taken for fasting plasma insulin and HbA1c. Insulin was analysed with rat insulin radioimmuno assay (RIA) (Crystalchem, IL). Blood (10 μl) for HbA1c determination was transferred to tubes with 1 ml hemolyzing agent (Roche A/S Diagnostics, Mannheim, Germany), frozen on dry ice and stored at −80° C. until analysis on a Hitachi 912 analyzer (Roche A/S Diagnostics, Mannheim, Germany) according to the manufacturer's instructions.

The results obtained are shown in FIG. 10 and FIG. 11.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (for example, "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents. The mentioning herein of references is no admission that they constitute prior art.

Herein, the word "comprise" is to be interpreted broadly meaning "include", "contain" or "comprehend" (vide, EPO guidelines C, III, 4.13).

This invention includes all modifications and equivalents of the subject matter recited in the claims and clauses appended hereto as permitted by applicable law.

What is claimed is:

1. A compound comprising the formula X—Y—Z, wherein X designates a calcitonin gene-related peptide (CGRP) compound from which, formally, a hydrogen has been removed from one of the amino groups present in an amino acid residue; Y is a linker elected from the group consisting of the six groups of the following formulae:

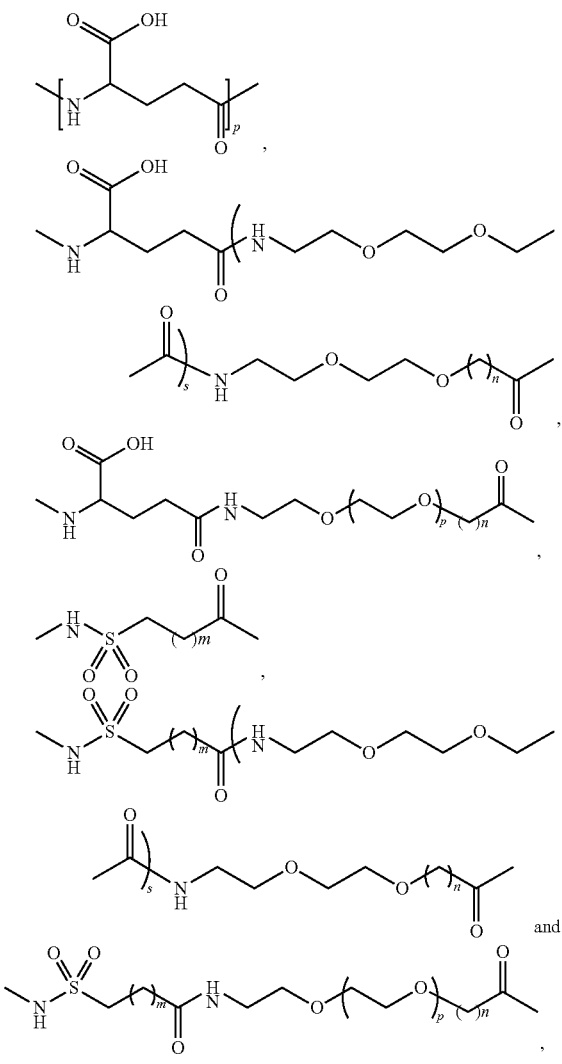

wherein m is 0, 1, 2, 3, 4, 5 or 6; n is 1, 2 or 3; s is 0, 1, 2 or 3; and p is 1, 2, 3, 4, 5, 6, 7, 8, 9, 10, 11, 12, 13, 14, 15, 16, 17, 18, 19, 20, 21, 22 or 23, and wherein the carbonyl end of these moieties is connected to the CGRP compound (designated X) and the amino end of these moieties is connected to the acyl group (designated Z); and Z is an acyl group; wherein the —Y—Z moiety is connected to an amino group present at the N terminal amino acid residue of the CGRP compound.

2. The compound according to claim 1, wherein the acyl group of Z originates from a fatty acid or fatty diacid with 12-22 carbon atoms.

3. The compound according to claim 2, wherein the acyl group present in Z originates from a fatty diacid with 12-22 carbon atoms.

4. The compound according to claim 1, wherein the CGRP compound has the general formula I (SEQ ID NO: 3):

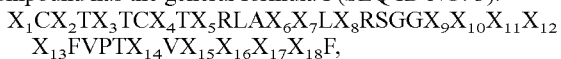

wherein $X_1$ is Ala or Ser, $X_2$ is Asp or Asn, $X_3$ is Ala or Ser, $X_4$ is Val or Ala, $X_5$ is His or Gln, $X_6$ is Gly or Asp, $X_7$ is Leu or Phe, $X_8$ is Ser, Asn or Arg, $X_9$ is Val, Ile, Met or Leu, $X_{10}$ is Val, Ala, Leu or Gly, $X_{11}$ is Lys, Ser, Asn or His, $X_{12}$ is Ser, Asn, Asp, Pro, $X_{13}$ is Asp or Asn, $X_{14}$ is Asp or Asn, $X_{15}$ is Gly or Ser, $X_{16}$ is Ala or Ser, $X_{17}$ is Glu, Gln, Lys or Asn, $X_{18}$ is Ala or Ser, and the carboxy group in the C terminal amino acid residue is, optionally, amidated, and, in formula I, the specific amino acid residues are indicated by the usual one letter codes for the amino acids; and said CGRP compounds have the usual intramolecular disulphide bridge between the two Cys residues.

5. The compound according to claim 1, wherein the CGRP compound has the general formula II (SEQ ID NO: 4):

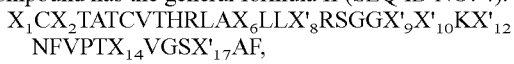

wherein $X_1$ is Ala or Ser, $X_2$ is Asp or Asn, $X_6$ is Asp or Gly, $X'_8$ is Arg or Ser, $X'_9$ is Val or Met, $X'_{10}$ is Val or Leu, $X'_{12}$ is Asp, Asn or Ser, $X_{14}$ is Asp or Asn, $X'_{17}$ is Glu or Lys, and the carboxy group in the C terminal amino acid residue is, optionally, amidated.

6. The compound according to claim 1, wherein the N terminal amino acid residue is a serine residue.

7. The compound according to claim 1, wherein the moiety of the formula —Y—Z is connected to the CGRP compound at a lysine residue.

8. The compound according to claim 7, wherein the lysine residue is selected from the group consisting of position 24 or position 35.

9. A composition comprising the compound of claim 1 and a pharmaceutically acceptable excipient.

10. The compound according to claim 4, wherein said CGRP compounds have the usual intramolecular disulphide bridge between Cys residue at position 2 and Cys residue at position 7.

11. A method of treatment of diabetes, insulin resistance, obesity, hypertension and cardiovascular disease, the method comprising administering to a subject in need thereof a therapeutically effective amount of a compound according to claim 1.

* * * * *